US012156735B2

United States Patent
Aluf et al.

(10) Patent No.: US 12,156,735 B2
(45) Date of Patent: Dec. 3, 2024

(54) DETECTION OF COGNITIVE STATE OF A DRIVER

(71) Applicant: ADAM COGTECH LTD., Beit Yehoshua (IL)

(72) Inventors: Erez Aluf, Beit Yehoshua (IL); Lidror Troyansky, Givataim (IL)

(73) Assignee: ADAM COGTECH LTD., Beit Yehoshua (IL)

( * ) Notice: Subject to any disclaimer, the term of this patent is extended or adjusted under 35 U.S.C. 154(b) by 479 days.

(21) Appl. No.: 17/422,555

(22) PCT Filed: Jan. 22, 2020

(86) PCT No.: PCT/IL2020/050084
§ 371 (c)(1),
(2) Date: Jul. 13, 2021

(87) PCT Pub. No.: WO2020/152678
PCT Pub. Date: Jul. 30, 2020

(65) Prior Publication Data
US 2022/0095975 A1    Mar. 31, 2022

Related U.S. Application Data

(60) Provisional application No. 62/795,039, filed on Jan. 22, 2019.

(51) Int. Cl.
*A61B 5/18*    (2006.01)
*A61B 3/14*    (2006.01)
(Continued)

(52) U.S. Cl.
CPC .............. *A61B 5/18* (2013.01); *A61B 3/14* (2013.01); *A61B 5/163* (2017.08); *A61B 5/165* (2013.01);
(Continued)

(58) Field of Classification Search
None
See application file for complete search history.

(56) References Cited

U.S. PATENT DOCUMENTS 7,648,366 B1 *   1/2010  Poulsen ................ G09B 9/003
                                                         434/236
2006/0132319 A1   6/2006  Isaji et al.
(Continued)

FOREIGN PATENT DOCUMENTS

JP    2006-158740 A    6/2006
JP    2007295946 A    11/2007
(Continued)

OTHER PUBLICATIONS

Jo [Vision-based method for detecting driver drowsiness and distraction in driver monitoring system, Optical Engineering 50(12), 127202 (Dec. 2011) ]. (Year: 2011).*
(Continued)

*Primary Examiner* — Oommen Jacob
(74) *Attorney, Agent, or Firm* — Tutunjian & Bitetto. P.C.

(57) ABSTRACT

A method, a system, an apparatus and a computer program product, for detecting and monitoring cognitive capabilities pertain to driving. The method comprises applying a series of stimuli on a driver while is driving a vehicle. The series of stimuli comprises a first portion matching a pattern and a second portion deviating from the pattern, and configured to induce an ocular response from eyes of the driver. The method further comprises obtaining a set of images of the eyes of the driver, that are captured during the application of the series of stimuli. The method further comprises analyzing the set of images to determine a set of ocular features corresponding each image; and determining, based thereon, a cognitive state of the driver. Based on the cognitive state
(Continued)

of the driver, a determination whether the driver is capable of operating the vehicle safely may be performed.

4 Claims, 13 Drawing Sheets

(51) Int. Cl.
| | |
|---|---|
| *A61B 5/00* | (2006.01) |
| *A61B 5/16* | (2006.01) |
| *B60W 30/14* | (2006.01) |
| *B60W 40/08* | (2012.01) |
| *B60W 50/14* | (2020.01) |
| *B60W 60/00* | (2020.01) |
| *G06N 20/00* | (2019.01) |
| *G06V 10/764* | (2022.01) |
| *G06V 10/774* | (2022.01) |
| *G06V 20/59* | (2022.01) |
| *G06V 40/16* | (2022.01) |
| *G06V 40/18* | (2022.01) |

(52) U.S. Cl.
CPC .......... *A61B 5/4884* (2013.01); *A61B 5/7267* (2013.01); *B60W 30/146* (2013.01); *B60W 40/08* (2013.01); *B60W 50/14* (2013.01); *B60W 60/0051* (2020.02); *G06N 20/00* (2019.01); *G06V 10/764* (2022.01); *G06V 10/774* (2022.01); *G06V 20/597* (2022.01); *G06V 40/18* (2022.01); *B60W 2540/22* (2013.01); *B60W 2540/221* (2020.02); *G06V 40/174* (2022.01)

(56) References Cited

U.S. PATENT DOCUMENTS

| | | | | |
|---|---|---|---|---|
| 2007/0132950 | A1* | 6/2007 | Victor | A61B 3/1015 |
| | | | | 351/200 |
| 2010/0109881 | A1* | 5/2010 | Eskandarian | B60K 28/066 |
| | | | | 340/576 |
| 2010/0214105 | A1* | 8/2010 | Manotas, Jr. | A61B 5/18 |
| | | | | 348/148 |
| 2012/0159656 | A1* | 6/2012 | Gerber | A61B 5/374 |
| | | | | 800/3 |
| 2013/0090562 | A1* | 4/2013 | Ryan | G16H 50/30 |
| | | | | 600/473 |
| 2013/0188838 | A1 | 7/2013 | Tsou et al. | |
| 2013/0295016 | A1* | 11/2013 | Gerber | A61K 49/0004 |
| | | | | 424/9.2 |
| 2014/0347265 | A1* | 11/2014 | Aimone | H04W 4/30 |
| | | | | 345/156 |
| 2016/0167672 | A1* | 6/2016 | Krueger | G16H 40/63 |
| | | | | 340/576 |
| 2016/0354023 | A1* | 12/2016 | Falck | A61B 5/38 |
| 2018/0184974 | A1* | 7/2018 | Cimenser | A61B 5/38 |
| 2018/0188807 | A1* | 7/2018 | Cimenser | A61B 5/18 |
| 2021/0113139 | A1* | 4/2021 | Hiratsuka | A61B 5/378 |

FOREIGN PATENT DOCUMENTS

| | | |
|---|---|---|
| JP | 2009-232945 A | 10/2009 |
| JP | 2014-191474 A | 10/2014 |
| WO | 2018049041 A1 | 3/2018 |

OTHER PUBLICATIONS

Tianchi Liu, et al., Driver Distraction Detection Using Semi-Supervised Machine Learning, IEEE Transactions on Intelligent Transportation Systems, Apr. 4, 2015, pp. 1108-1120, vol. 17, No. 4, Apr. 2016.
International Search Report from PCT/IL2020/050084 dated Feb. 19, 2020, 4 pgs.
Japanese Examination Report from Japanese Application No. 021-543307 dated Feb. 21, 2024, 5 pgs.
Israeli Office Action from Israeli Application No. 284881 dated Dec. 31, 2023, 7 pgs.

* cited by examiner

DETECTION OF COGNITIVE STATE OF A DRIVER

CROSS-REFERENCE TO RELATED APPLICATIONS

This application claims the benefit of U.S. provisional Application No. 62/795,039 filed Jan. 22, 2019, which is hereby incorporated by reference in its entirety, without giving rise to disavowment.

TECHNICAL FIELD

The present disclosure relates to cognitive state detection in general, and to monitoring cognitive capabilities pertain to driving, in particular.

BACKGROUND

Car accidents are responsible for a substantial fraction of morbidity and mortality in the modern world.

Human factors are a major cause of such car accidents. A large number of car accidents stem from the fact that, in many cases, drivers do not have the capabilities that are required for an effective driving: Some of the human factors are related to cognitive state that can reduce driving capability, such as drowsiness, fatigue, alcohol intoxication, drug effects, acute psychological stress, emotional distress, temporary distraction, and the like. Such cognitive state may reduce the ability of the driver to overcome road hazards.

BRIEF SUMMARY

One exemplary embodiment of the disclosed subject matter is a method comprising: applying a series of stimuli on a driver, wherein said applying is performed while the driver is driving a vehicle, wherein the series of stimuli comprises a first portion matching a pattern and a second portion deviating from the pattern, wherein the series of stimuli is configured to induce an ocular response from eyes of the driver; obtaining a set of images of the eyes of the driver, wherein the set of images are captured during the application of the series of stimuli; analyzing the set of images to determine a set of ocular features corresponding each image; and determining, based on the set of ocular features of the set of images, a cognitive state of the driver.

Optionally, the method further comprises: determining, based on the cognitive state of the driver, whether the driver is capable of operating the vehicle safely.

Optionally, the method further comprises: determining whether the cognitive state of the driver is above a minimal threshold; and in response to a determination that the cognitive state is below the minimal threshold, performing a responsive action.

Optionally, the set of ocular features comprises at least one of: a saccade of at least one eye of the eyes; a size of at least one pupil of the eyes; a dilation response of at least one eye of the eyes; a constriction response of at least one eye of the eyes; a symmetry measurement between the eyes; a facial expression in a proximity of the eyes; and an eyebrow movement.

Optionally, said determining the cognitive state is performed based on one or more statistical measurements of the set of ocular features of the set of images.

Optionally, the series of stimuli is determined based on properties of the driver, wherein said determining the cognitive state is further performed based on the properties.

Optionally, said determining the cognitive state is performed using a classifier, wherein the classifier is trained with respect to a set of measurement obtained by monitoring the driver.

Optionally, said determining the cognitive state is performed using a classifier, wherein the classifier is trained with respect to a set of measurement obtained by monitoring one or more different drivers having a similarity measurement below a threshold to the driver, wherein the classifier is trained without monitored data of the driver.

Optionally, the second portion deviating from the pattern deviates from the pattern in at least one of a timing of stimulus, a spatial location of stimulus, a magnitude of stimulus, and a type of stimulus.

Optionally, the series of stimuli comprises a plurality of stimuli from the first portion, followed by an oddball stimulus from the second portion that deviates from the pattern, wherein the plurality of stimuli from the first portion is a sequence of stimuli that match the pattern, wherein the pattern comprises at least a temporal pattern.

Optionally, the series of stimuli comprises as at least one of: visual stimuli, audible stimuli, and haptic stimuli.

Optionally, the set of images is obtained from one or more sensors located within the vehicle and facing the driver.

Optionally, said determining the cognitive state is further performed based on driving data of the driver, wherein the driving data is obtained from a computing device of the vehicle.

Optionally, the set of images is obtained from a Driver Monitoring System (DMS) of the vehicle.

Optionally, the method further comprises: in response to determining that the cognitive state of the driver is not compatible with safe driving requirements, alerting a controller system of the vehicle.

Optionally, the controller system is configured to perform, in response to said alerting, a limiting action, wherein the limiting action comprises at least one of: activating autonomous driving of the vehicle; limiting a speed of the vehicle; instructing the vehicle to make a safe stop; issuing an alert to a third party; and issuing an alert to the driver.

Optionally, said applying comprises: determining the series of stimuli; and providing each stimulus of the series of stimuli using an output device that is located in the vehicle and directed at the driver.

Another exemplary embodiment of the disclosed subject matter is a method comprising: obtaining a set of images of eyes of a driver, wherein the set of images is captured while the driver is exposed to a series of stimuli and while the driver is driving a vehicle, wherein the series of stimuli comprises a first portion matching a pattern and a second portion deviating from the pattern, wherein the series of stimuli is configured to induce an ocular response from the eyes, wherein the series of stimuli is occurring, at least in part, naturally in a viewing scene of the driver; analyzing the set of images to determine a set of ocular features corresponding each image; and determining, based on the set of ocular features of the set of images, a cognitive state of the driver.

Optionally, the method further comprises utilizing a visual sensor to capture the viewing scene of the driver, and analyzing the viewing scene to determine the naturally occurring portion of the series of stimuli.

Optionally, the series of stimuli is partially naturally occurring, and wherein the method further comprises providing an augmented view of the viewing scene to cause the driver to view the series of stimuli.

Optionally, the first portion of the series of stimuli comprises existing visual stimuli in the viewing scene of the driver, wherein the pattern is determined based on elements in the existing visual stimuli, wherein the second portion of the series of stimuli is dynamically generated using augmented reality to deviate from the pattern in the existing visual stimuli, whereby minimizing intervention on sight of the driver.

Yet another exemplary embodiment of the disclosed subject matter is a computerized apparatus having a processor, the processor being adapted to perform the steps of: applying a series of stimuli on a driver, wherein said applying is performed while the driver is driving a vehicle, wherein the series of stimuli comprises a first portion matching a pattern and a second portion deviating from the pattern, wherein the series of stimuli is configured to induce an ocular response from eyes of the driver; obtaining a set of images of the eyes of the driver, wherein the set of images are captured during the application of the series of stimuli; analyzing the set of images to determine a set of ocular features corresponding each image; and determining, based on the set of ocular features of the set of images, a cognitive state of the driver.

Yet another exemplary embodiment of the disclosed subject matter is a computer program product comprising a non-transitory computer readable storage medium retaining program instructions, which program instructions when read by a processor, cause the processor to perform a method comprising: applying a series of stimuli on a driver, wherein said applying is performed while the driver is driving a vehicle, wherein the series of stimuli comprises a first portion matching a pattern and a second portion deviating from the pattern, wherein the series of stimuli is configured to induce an ocular response from eyes of the driver; obtaining a set of images of the eyes of the driver, wherein the set of images are captured during the application of the series of stimuli; analyzing the set of images to determine a set of ocular features corresponding each image; and determining, based on the set of ocular features of the set of images, a cognitive state of the driver.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings:

FIGS. 7A-7C show flowchart diagrams of a method, in accordance with some exemplary embodiments of the disclosed subject matter.

DETAILED DESCRIPTION

Figure 1:
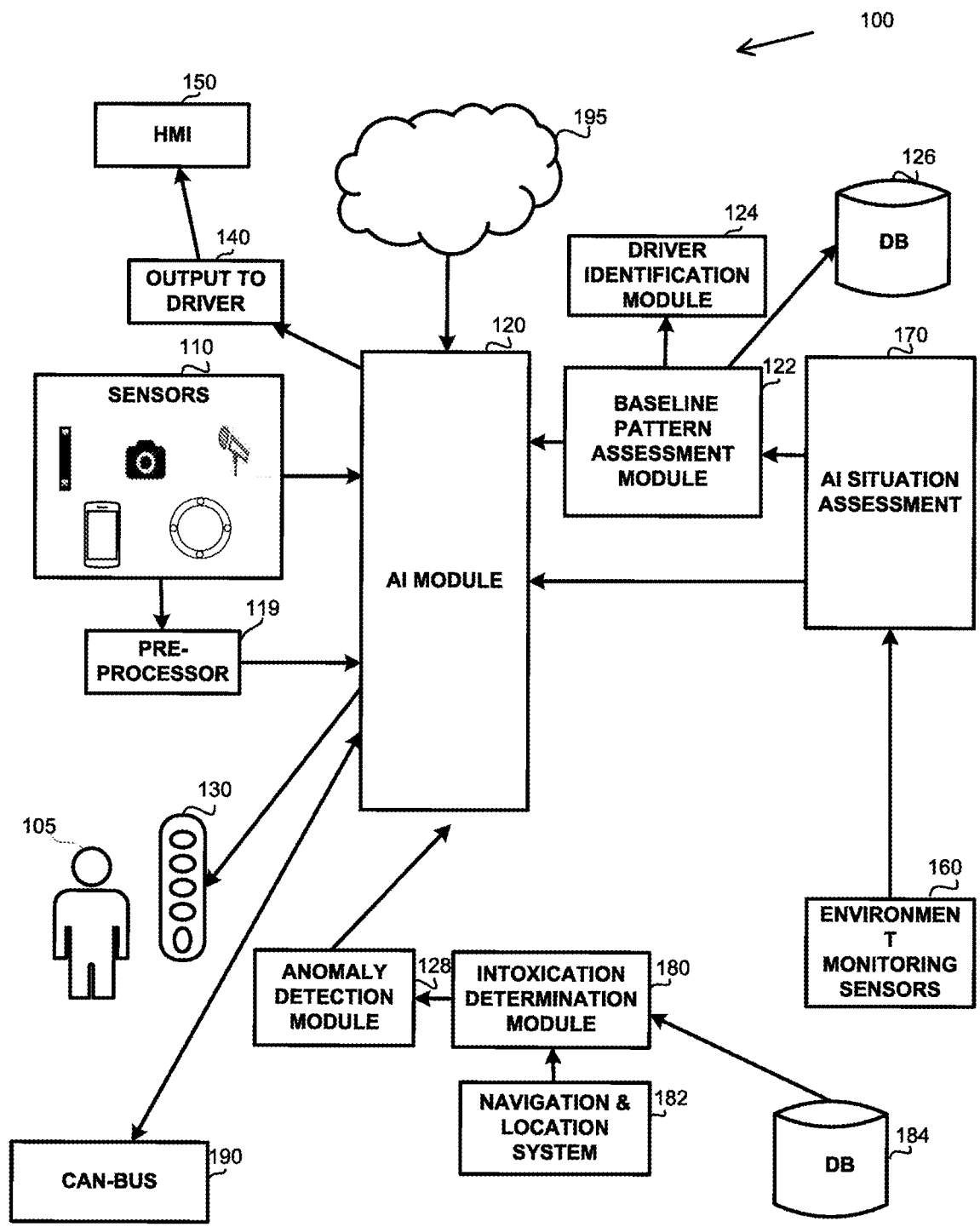
FIG. 1 shows a schematic illustration of an exemplary architecture of a system, in accordance with some exemplary embodiments of the disclosed subject matter.

One technical problem dealt with by the disclosed subject matter is to detecting cases in which the driver is not capable to conduct a safe driving. In some exemplary embodiments, the cognitive state of drivers may affect the quality of their driving. Deterioration of the cognitive state, such as because of consumption of alcohol or drugs, fatigue, emotional stress, or the like, may reduce the capability of drivers to conduct a safe driving, and may even risk with fatal car accidents.

In some exemplary embodiments, monitoring driving capabilities of drivers may be performed by monitoring driving behavior thereof, such as deviation from the driving lane, abrupt stops, turning with a wide radius, driving on the center lane marker or the roadside marker, or the like. Other methods may include cameras and processing systems that may alert about drowsiness, such as by counting the frequency and the duration of eye-blinks, monitoring whether the eyes of the driver are looking at the road, or the like. However, such method may fail to assess and predict the cognitive state of the driver or deterioration thereof resulted from alcohol or drug consumption, fatigue, emotional stress, or the like. Additionally or alternatively, such methods may not be capable of detecting risky cognitive state at early stages before attempting hazardous driving behavior, that may already risk lives.

One technical solution is to continuously monitor the cognitive state of the driver by actively applying stimuli on the driver and passively monitoring ocular response of the driver.

In some exemplary embodiments, a series of stimuli operable of inducing ocular response from the driver eyes may be applied on the driver. The series of stimuli may be applied on the driver while the driver is driving a vehicle. The series of stimuli may comprise a first portion matching a pattern and a second portion deviating from the pattern. Stimuli from the second portion, which deviate from the pattern, may be configured to induce a different brain activity than the brain activity induced by stimuli matching the pattern. As a result, the series of stimuli may be configured to induce an ocular response by the eyes of the driver that correlates with the induced different brain activity.

In some exemplary embodiments, the stimuli may be visual stimuli, that may be displayed on a head up display, the middle mirror in the vehicle, the sun visor, the windshield, on a center console in the vehicle, the steering wheel, or the like. Additionally or alternatively, the stimuli may be audible stimuli, that may be provided by the in-car entertainment or infotainment system of the vehicle, using an instrument cluster, using a microphone placed in the vehicle, via the driver's computing device, or the like. Additionally or alternatively, the stimuli may be haptic stimuli, applied by the steering wheel, the driver seat, the seat belt, or the like. Additionally or alternatively, the stimuli may be provided by a combination of modalities: visual, auditory or haptic.

It may be noted that the applied stimuli may not affect the driving quality of the driver, or other physical or mental functioning thereof, or the like. In some embodiments, a subliminal set of stimuli that do not increase the cognitive load on the driver may be utilized, thereby improving the driver's experience. As an example, visual stimuli may be with various levels of saliency, such as for a short duration (about 100 milliseconds, about 1.5 seconds, or the like), in the peripheral area of the driver visual field, or the like. As another example, audio stimuli may be provided as a barely noticeable audio signal provided in different directions to produce a pattern. The barely noticeable audio signal may be adapted with the driver's preference, the driver's environment, or the like. The barely noticeable audio signal may be based on manipulating the environmental sounds detected by system acoustic sensors, such as by adding a noise with similar characteristics and modulating the amplitude for short periods while monitoring the driver's reaction. As another example, haptic stimuli may be provided by a tactile module embedded in the driver's seat or steering wheel to introduce haptic stimuli in different levels of magnitude.

In some exemplary embodiments, behavior of the driver eyes may be monitored to determine a set of series of ocular responses in accordance with the set of time-series stimuli. The monitoring may be performed passively using sensors located within the vehicle and facing the driver. A set of images of the eyes of the driver, as captured during the application of the series of stimuli, immediately after the application, or the like, may be obtained from the sensors. The set of images may be analyzed to determine a set of ocular features corresponding each image. In some exemplary embodiments, the set of ocular features may comprise features that are affected by a brain activity associated with a surprise, such as features related to saccadic eye movements, features related to the size of the pupil and dilation response, constriction responses, symmetry measurement between the eyes, facial expressions in a proximity of the eyes, eyebrows movement, or the like.

In some exemplary embodiments, the determination of the cognitive state may be performed based on one or more statistical measurements of the set of ocular features of the set of images. As an example, the one or more statistical measurements may be applied on the set of ocular features to generate a set of uncorrelated variables, a smaller dimension of feature vector, or the like.

In some exemplary embodiments, the set of ocular features may be analyzed to determine the cognitive state of the driver. A determination whether the driver is capable of a safe driving may be performed based on the cognitive state thereof. In response to determining that the cognitive state of the driver is not compatible with safe driving requirements, a controller system of the vehicle may be alerted. The controller system may be configured to perform a limiting action such as activating autonomous driving of the vehicle, issuing an alert to the driver or to a third party, or the like.

In some exemplary embodiments, a dynamic control algorithm may be utilized to determine a positive or a negative reward to the driver to alter the cognitive state of the driver in order of to comply with the situation and to facilitate an adaptive response. In some exemplary embodiments, the reward may be determined so as to improve the quality of the driver's response within the long term. In some embodiments, reinforcement and rewards to the drivers may comprise positive and negative reinforcement, operable to condition the driver and to improve the compatibility of the cognitive state of the driver to the desired ones. In some embodiments, negative rewards may be induced using low saliency noise and destructions that would make drivers feel slightly uncomfortable when their reaction to the stimuli significantly deviates from an optimal one. In some embodiments, long-term positive rewards include virtual tokens that can be translated to various digital goods or to discounts for shopping or dining, while long-term negative rewards may be obtained by reducing the number of such virtual tokens in the driver's account. In some embodiments, a gamification paradigm is used to provide positive and negative reinforcement as a part of a game. In some embodiments, reinforcement may be coupled with subliminal stimulus to create seamless and non-intrusive shaping of driver's behavior. This may be used to maintain driver's cognitive state at a specific level while minimizing unnecessary perceptual load.

Another technical solution is to monitor stimuli naturally occurring on the viewing scene of the driver while driving, and continuously monitor the cognitive state of the driver by passively monitoring ocular response of the driver in response to the stimuli.

In some exemplary embodiments, the viewing scene of the driver while driving the vehicle may comprise element that may seem like a series of stimuli, such as repetitive objects on the road, repetitive markings, or the like. The viewing scene may even comprise objects or events that may cause a breaking of the pattern, such as a sign appearing in a while, a missing object, an object in different size or with different distance, or the like. Such stimuli may be utilized instead of dynamically generated stimuli, to inspect the ocular response of the driver.

Additionally or alternatively, only a portion of the series of stimuli may be occurring, naturally in a viewing scene of the driver. In such cases, augmented reality techniques may be utilized to induce the missing stimuli in the viewing scene, whereby minimizing intervention on sight of the driver.

In some exemplary embodiments, the viewing scene of the driver may be captured by one or more visual sensor, such as smart cameras on the windshield, dashboard cameras, video recorders on the vehicle front, road cameras, or the like. Computer vision techniques may be applied to analyze the viewing scene and determine the naturally occurring portion of the series of stimuli. Using AI and machine learning techniques, the missing portion of the series of stimuli may be determined, and an augmented view of the viewing scene may be generated to cause the driver to view the series of stimuli as whole. It may be appreciated to minimize the portion added by augmented reality in order minimize the intervention on sight of the driver.

One technical effect of utilizing the disclosed subject matter is preventing fatigue car accidents resulting for detrition of cognitive state of drivers. The disclosed system enables continuously monitoring the cognitive state of the driver during the driving, and in response to determining that the cognitive state of the driver is not compatible with safe driving requirements, alerting a controller system of the vehicle to perform a limiting action that may prevent a potential accident.

Another technical effect of utilizing the disclosed subject matter is monitoring the cognitive state of the driver, during driving, in a minimally intrusive manner. Monitoring the cognitive state in the disclosed method is performed without affecting her driving, or her other cognitive abilities. The disclosed system generates a set of stimuli tailored for the driver. Saliency and content of the stimuli are designed to be compatible with the environmental condition and the urgency level of the situation, such as the severity of the cognitive state, the risk associated therewith, or the like.

Yet another technical effect of utilizing the disclosed subject matter is enhancing the efficacy and effectiveness of cognitive state monitoring without increasing the load on the driver. By utilizing stimuli naturally occurring in the viewing scene of the driver, the disclosed system minimizes the intervention on the brain activity of the driver.

The disclosed subject matter may provide for one or more technical improvements over any pre-existing technique and any technique that has previously become routine or conventional in the art. Additional technical problem, solution and effects may be apparent to a person of ordinary skill in the art in view of the present disclosure.

Referring now to FIG. 1 showing a schematic illustration of an exemplary architecture of a system, in accordance with some exemplary embodiments of the disclosed subject matter.

In some exemplary embodiments, a System 100 may be utilized for assessing cognitive state of drivers during driving a vehicle.

In some exemplary embodiments, System 100 may comprise one or more Sensors 110 for monitoring a Driver 105. Sensors 110 may be aimed at Driver 105 to monitor her behavior. Sensors 110 may comprise an eye tracker for the eyes of Driver 105, 112, an inward looking camera, pressure sensors on a wheel of the vehicle, a microphone, an Infrared (IR) sensor, a combination thereof, or the like. Sensors 110 may be configured to continuously monitor Driver 105, especially the eyes of Driver 105. Sensors 110 may be configured to collect data operable to create indicators regarding the cognitive state of Driver 105. Such data may comprise ocular features associated with Driver 105.

In some exemplary embodiments, System 100 may comprise an Artificial Intelligence (AI) Module 120 for evaluation of the cognitive state of Driver 105. AI Module 120 may be configured to compile various observables and indicators from different sources in order to assess the cognitive state of Driver 105. AI Module 120 may be configured to utilize various AI methods and techniques such as deep learning, Artificial Neural Networks (ANN), multilayer Convolutional Neural Networks (CNN), or the like, to analyze indicators in images of Driver 105$m$ such as facial expression, the eye movements, gaze direction, pupil dilation, behavioral patterns, or the like. AI Module 120 may be configured to transform the indicators into higher level indicators that provide information regarding the basic computational capabilities of Driver 105.

In some exemplary embodiments, System 100 may comprise a Probing Module 130 configured to probe Driver 105, display stimuli for Driver 105, display alerts for Driver 105, or the like. Probing Module 130 may be located in the vehicle facing Driver 105, such as on a screen, a windshield, steering wheel, middle mirror, or the like. In some exemplary embodiments, Probing Module 130 may be operable to work on the subliminal level or the barely perceptible level, thereby providing a minimal level of interference to the normal operation of Driver 105. In some exemplary embodiments, Probing Module 130 may be configured to apply various stimuli on Driver 105. The reaction of Driver 105 to the stimuli may be monitored by Probing Module 130, by one or more sensors from Sensors 110, or the like. The reaction of Driver 105 may be provided to AI Module 120, to determine a cognitive state of Driver 105.

In some exemplary embodiments, System 100 may comprise a Communication Module 140 that is configured to communicate with Driver 105, provide additional output to Driver 105, or the like. Communication Module 140 may be configured to communicate with Driver 105 via a Human Machine Interface (HMI) module 150. The outputs to Driver 105 may comprise indication regarding her cognitive state, suggestions for safe driving, recommendations, alerts, hints, required actions, such as stopping for rest, slowing down, or the like, or the like.

In some exemplary embodiments, System 100 may be personally tailored to Driver 105, taking into account her physical condition in general, such as based on demographic and physical data thereof, such as age, acuity of sight, or the like. Additionally or alternatively, physical and mental condition of Driver 105 at each specific time may be determined, such as fatigue, alertness, mood, destructions, or the like. Additionally or alternatively, the dynamics of ongoing attention allocation. System 100 may continuously monitor the cognitive state and behavior of Driver 105, probe the Driver 105 with a potentially tailored set of stimuli, and analyze the responses to the stimuli.

In some exemplary embodiments, System 100 may comprise AI Situation Assessment Module 170. AI Situation Assessment Module 170 may be configured to analyze data obtained from Environment Monitoring Sensors 160, and provide processes related data to AI Module 120. Environment Monitoring Sensors 160 for monitoring the drive in front of the vehicle, viewing scenes seen by Driver 105, or the like. Environment Monitoring Sensors 160 may be configured to collect information about the environment regarding the context and the situation, such as properties of the road, interaction with other drivers, vehicles or objects, signs, capturing the viewing scene in front of Driver 105, or the like. Environment Monitoring Sensors 160 may comprise a multispectral camera, operable to assess physiological parameters such as body temperature and pulse and to penetrate sunglasses, cameras utilizing infrared images, digital cameras, video recorders, or the like. AI Situation Assessment Module 170 may be configured to compile observable and indicators from Environment Monitoring Sensors 160. The observable and indicator may comprise observables and indicators regarding road conditions, hazards, potential threats, destructions from the inside and the outside of the vehicle and other observables that may be relevant or affect the performance of Driver 105 or the vehicle, or the like. AI Module 120 may be configured to apply methods such as deep learning, Bayesian networks, or the like, in order to combine the various observables and indicators and assess the situation and the context, thereby infer cases in which there are incompatibility between the state and the action of Driver 105 and the actual situation.

Additionally or alternatively, System 100 may comprise an Intoxication Determining Module 180, that is configured to estimate a consumption of alcohol or drugs by Driver 105. Intoxication Determining Module 180 may be connected to a Navigation and Location System 182, and a Database 184. Navigation and Location System 182 may be configured to determine location information of Driver 105, such as using Global Positioning System (GPS) or other location sensors, along with other data from a Database 184 pertaining to locations of potential problematic locations, such as rehabilitation centers, entertainment venues serving alcohol, or the like. Intoxication Determining Module 180 may be configured to assess the likelihood that Driver 105 might have consumed alcohol or drugs. The likelihood may be used by AI Module 120, together with a corresponding margin of confidence, in order to adjust the sensitivity level of the AI Module 120.

Additionally or alternatively, System 100 may comprise a Baseline Pattern Assessment Module 122 configured to determine behavioral patterns and historical data of Driver 105, to assist AI Module 120 in determining the cognitive state of Driver 105. Baseline Pattern Assessment Module 122 may be configured to utilize a Driver Identification Module 124 for identifying Driver 105 and properties thereof, such as based on biometric data of Driver 105, such as face recognition using a monitoring camera from Sensors 110, fingerprint or handprint using sensors on the wheel from Sensors 110, or the like. Additionally or alternatively, Driver Baseline Pattern Assessment Module 122 may obtain data based on the identity of Driver 105 from local Database 126, external databases, the Internet or the like. Such data may comprise behavioral patterns of Driver 105, historical data of Driver 105, driving patterns of Driver 105, traffic tickets, or the like. The data may be analyzed by Baseline Patterns Assessment module 122 to determine driving patterns of Driver 105. The patterns may comprise driving patterns in various locations and conditions, ocular responses in various situations and conditions, ocular responses to stimuli, or the like. The patterns may be stored in Database 126, in the cloud, or the like. Additionally or alternatively, System 100 may comprise an Anomaly Detection Module 128 to detect anomalies that serve as indicators for the cognitive state of Driver 105. In some exemplary embodiments, the anomaly detection may be based on auto-encoder that is trained to reproduce the data using a lower dimension representation, and define such anomalies based on failure of such reproducing.

Additionally or alternatively, System 100 may comprise a Pre-Processing Unit 119 that is configured to process the data from Sensors 110 before being provided to AI Module 120. Pre-Processing Unit 119 may be configured to produce second-level features based on the data collected by Sensors 110. As an example, Pre-Processing Unit 119 may produce ocular features of Driver 105, such as a feature relating to gaze direction within the visible scene, a feature relating to pupil dilation, a feature indicative of a behavioral pattern that is indicative of low receptivity levels, or the like. In some embodiments, Pre-Processing Unit 119 may be configured to utilize a prediction model, such as an Auto-Regressive (AR) model, Kalman filter, particle filter, deep neural networks with Long-Short Term Memory, a combination thereof, or the like, in order to calculate the second-level features. The prediction model may be utilized to determine features that are related directly to the cognitive state of Driver 105, based on the second-level features or the ocular features. As an example, Pre-Processing Unit 119 may be configured to predict the focus of the attention of the Driver 105. AI Module 120 may be configured to transform the second-level features or the direct features into a vector of cognitive level indicators, together with a corresponding confidence level. In case of determining a cognitive state below a predetermined threshold, such as about 30% below the optimal level, with a confidence level that is above a second predetermined threshold, such as about 90%, 95%, or the like, System 100 may be configured to alert Driver 105 using Communication Module 140. Additionally or alternatively, in case the confidence level is below a third predetermined threshold, such as about 70%, 60%, 50%, or the like, System 100 may re-probe Driver 105 with a different series of stimuli using Probing Module 130 and monitor the reaction of Driver 105 to these stimuli by Sensors 110. AI Module 120 may be configured to generate a new set of receptivity level indicators, potentially with higher confidence levels.

Additionally or alternatively, AI Module 120 may be configured to apply an HMM in order to determine the cognitive state of Driver 105. As an example, the visible states of the HMM may comprise ocular features such as eye fixations on various object of interest within the visual field, and the hidden states may represent related cognitive features, such as allocating attention to objects and potential threats vs. merely looking or staring at the object while daydreaming, or the like. AI Module 120 may thereafter utilize HMM learning algorithms, such as the Baum-Welch algorithm, to assess the likelihood of transitions in order to assess the cognitive state of Driver 105, to predict next states, to determine the need to apply control stimulus, or the like.

Additionally or alternatively, Probing Module 130 may be configured to introduce stimuli whose saliency and content are compatible with the environmental condition and the urgency level of the situation (e.g., the severity of the cognitive state). The saliency of the stimulus may be determined by multiple parameters, such as modality, duration, strength, location, or the like. The saliency of the stimuli may be gradually increased while constantly monitoring the reaction of Driver 105 until the desired alert level is reached. Using this paradigm, System 100 may operate in a minimally intrusive manner.

Additionally or alternatively, System 100 may be connected to Controller Area Network (CAN-bus) 190 of the vehicle. CAN-bus 190 may be configured to provide indicators from the computer of the car, such as accelerations, lane-keeping, sudden braking, or the like. The indications may be utilized by AI Module 120 as additional indicators regarding the status of Driver 105. Additionally or alternatively, System 100 may issue signal to the vehicle computer via CAN-bus 190, to alter the parameters of the vehicle in cases in which the cognitive state of Driver 105 is not compatible with the environmental requirements, such as to limit the speed of the vehicle, instruct vehicle to change lanes, operate windshield wipers in vehicle to alert Driver 105, increase or decrease the volume of a media center, a radio or other entrainment system used by Driver 105 to increase her attention, or the like.

Additionally or alternatively, AI Module 120 may be configured to utilize data from the Cloud 195 to improve the assessment of the cognitive state. In some exemplary embodiments, Cloud 195 may provide information regarding ocular responses of other drivers in similar environment, thereby improving the assessment of the cognitive state of Driver 105. In some exemplary embodiments, environmental information external to the vehicle, such as up-to-date traffic information, information regarding other vehicles in the vicinity of the driver, weather information, or the like, may also be used to improve the quality of the decisions of AI Module 120.

Figure 2A:
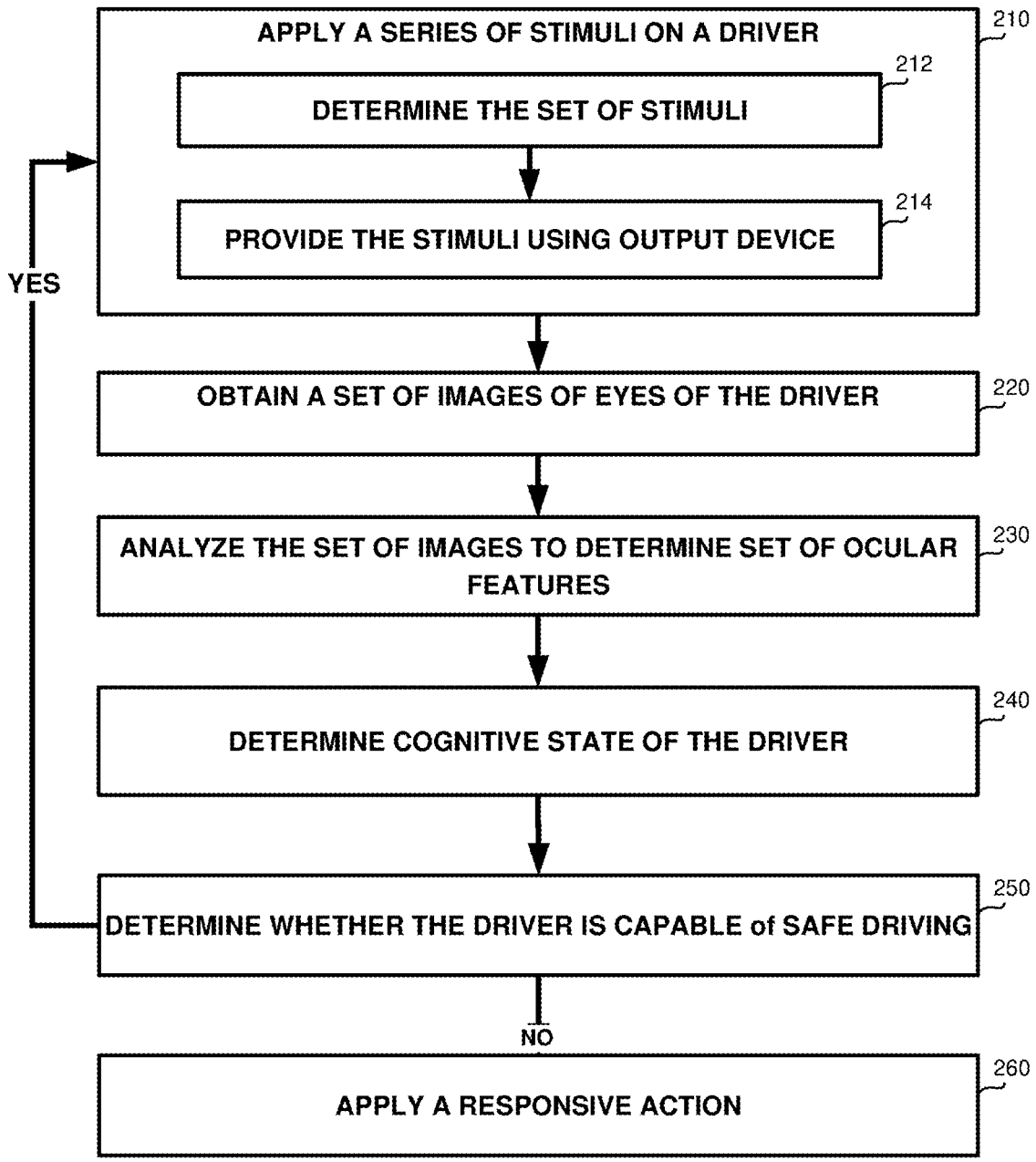
FIGS. 2A-2C show flowchart diagrams of a method, in accordance with some exemplary embodiments of the disclosed subject matter.

Referring now to FIG. 2A showing a flowchart diagram of a method, in accordance with some exemplary embodiments of the disclosed subject matter.

On Step 210, a series of stimuli may be applied on a driver while driving a vehicle. In some exemplary embodiments, the series of stimuli may comprise a first portion matching a pattern and a second portion deviating from the pattern. The series of stimuli may be arranged as a sequence of stimuli matching the pattern (e.g., from the first portion) and a stimulus breaking the pattern (e.g., from the second portion). Such breaking may be configured to induce a brain activity indicative of a surprising event which may be configured to induce a responsive ocular response from eyes of the driver. The plurality of stimuli from the first portion may be a sequence of stimuli that match a temporal pattern, a spatial pattern, or the like. In some exemplary embodiments, the second portion deviating from the pattern, may be configured to deviate from the pattern in a timing of stimulus, a spatial location of stimulus, a magnitude of stimulus, a type of stimulus, or the like. The deviation may be based on a paradigm of breaking the expected pattern, in a manner operable to induce certain brain activities. As an example, the stimuli may comprise displaying N consecutive images in the same location on a display, such as a screen, a windshield, or the like, and shifting the $N+1^{th}$ image into a new location. As another example, the series of stimuli may comprise temporal colored light stimuli in in a constant pace.

On Step 212, the series of stimuli may be determined based on properties of the driver. The series of stimuli may be tailored for each driver in accordance with the driver's properties, with environmental parameters, or the like.

In some exemplary embodiments, the series of stimuli may be tailored to the driver based on her physical condition in general, such as based on demographic features, assessed physical and mental condition, dynamics of ongoing attention allocation, or the like. In some exemplary embodiments, machine learning techniques may be applied in order to determine the series of stimuli based on such properties and parameters. As an example, control engineering and reinforcement learning may be utilized to provide an optimal set of stimuli to the driver.

In some exemplary embodiments, a type of the stimuli, e.g., visual, haptic, audible, a combination thereof, or the like, may be determined. Additionally or alternatively, the means of providing the stimuli, timing of each stimulus, a spatial location of stimulus, a magnitude of stimulus, a type of stimulus or the like, may be determined. Additionally or alternatively, the series of stimuli may be determined based on cognitive properties of the driver in a manner that minimizes effects of the stimuli on the driver cognitive activity, driving activity, or the like. As an example, some drivers may be more sensitive to stimulus than other drivers. Accordingly, less intervention stimuli or more natural stimuli may be applied thereon. As another example, if the stimuli is a visual que, such as a led that appears on the dashboard for a period of T seconds with a strength of X lumens, the system may assess the response time and the time of ocular fixation on the stimuli, in order to determine whether the above parameters T and X may provide an adequate set of control parameters for the stimuli, taking into account the general situation. The system may start with parameter values, such as X=50, X=60, X=100 lumens, or the like; and T=0.2, T=0.5, T=0.7 sec, or the like, and adapt them to the driver.

On Step 214, each stimulus of the series of stimuli may be provided using an output device that is located in the vehicle and directed at the driver. In some exemplary embodiments, the series of stimuli may be provided as visual stimuli, audible stimuli, haptic stimuli, a combination thereof, or the like. As an example, visual stimuli may be presented on a display on an instrument cluster, a steering wheel, a head up display, a vehicle mirror, a vehicle sun visor, a windshield, a center console, or the like. In some exemplary embodiments, the system may utilize existing visual elements as visual stimuli, and control such elements to introduce the deviation from the pattern. As an example, the movement of the wipers of the vehicle, which occur in a certain pace may be utilized as a visual stimuli having a certain pattern; that may be broke by changing the speed of the wipers, suddenly stopping the wipers, or the like. As another example, audible stimuli may be provided by the infotainment system, of the vehicle, using an instrument cluster, using a microphone placed in the vehicle, via the driver's mobile device, or the like. As yet another example, haptic stimuli may be applied by the steering wheel, the driver seat, the seat belt, as vibrations from the driver's mobile device, or the like.

On Step 220, a set of images of the eyes of the driver may be obtained. In some exemplary embodiments, the set of images may be captured during the application of the series of stimuli. Additionally or alternatively, the set of images may be taken in a predetermined time window following the application of the series of stimuli, such as 3 seconds following the application of the series of stimuli, 4 seconds, 10 seconds, or the like. The set of images may be obtained from one or more sensors located within the vehicle and facing the driver, such as an eye tracker, inward looking camera, a thermographic camera, IR sensors, or the like. The set of images may comprise a large number of images to enable a better analysis of the ocular responses therein, such as about 100 images, 400 images, 1000 images, or the like. Accordingly, sensors with adapted computational powers may be utilized, such as eye trackers capable of tracking about 100 frames/sec, about 150 frames/sec, about 200 frames/sec, or the like.

In some embodiments the sensors may comprise a multispectral camera, operable to assess physiological parameters of the subject such as body temperature, pulse, or the like. The sensors may be adapted to penetrate sunglasses, lenses, makeup, or the like, such as by utilizing IR images. Additionally or alternatively, the set of images may be obtained from a DMS of the vehicle, or other computing device of the vehicle connected to visual sensors capturing the eyes of the driver.

On Step 230, the set of images may be analyzed to determine a set of ocular features corresponding each image. In some exemplary embodiments, computer vision techniques, AI image processing techniques, object detection techniques, or the like, may be utilized to analyze the set of images and extract the relevant ocular features. In some exemplary embodiments, the set of ocular features may comprise features related to the eyes of the driver, that are associated with certain brain activity. The set of ocular features may comprise features related to the saccades of one or more of the eyes of the driver (such as accuracy of saccades, frequency of saccades, velocity of saccades, eye fixation time, or the like), a size of at least one pupil of the eyes, a dilation response of at least one eye of the eyes, a constriction response of at least one eye of the eyes, a symmetry measurement between the eyes, a facial expression in a proximity of the eyes, an eyebrow movement, or the like. In response to applying the series of stimuli, different ocular responses may be captured for surprising stimuli or oddballs, e.g., instances in which the pattern of the last few stimuli is broken.

In some exemplary embodiments, the features may be extracted both in the time domain, directly from the time series that represents, e.g., the coordinates of the point of gaze at various times and from the power spectrum of the time series.

On Step 240, a cognitive state of the driver may be determined based on the set of ocular features of the set of images. In some exemplary embodiments, the cognitive state at a certain time point may be indicative of the maximal capacity of the driver to be engaged in the driving activity. In some exemplary embodiments, the cognitive state may be determined based on one or more statistical measurements of the set of ocular features of the set of images. The statistical measurements may comprise an Independent Component Analysis (ICA) measurement, a Principal Component Analysis (PCA) measurement, an entropy measurement, Nonparametric Weighted Feature Extraction (NWFE) measurement, Gaussian Maximum Likelihood (GML) measurement, k-Nearest-Neighbor classifier (kNN) measurement, Standard Deviation (STD), average, mean, a combination thereof, or the like.

In some exemplary embodiments, the cognitive state of the driver may be determined using a classifier. In some exemplary embodiments, the classifier may be applied on the set of ocular features of the set of images. Additionally or alternatively, the classifier may be applied on the one or more statistical measurements of the set of ocular features of the set of images. Additionally or alternatively, the classifier may determine other features, such as but not limited to properties of the driver, such as demographic properties, such as age, gender, or the like, road conditions, driving habits, or the like. Additionally or alternatively, the determination may be further performed based on driving data of the driver, as obtained from a computing device of the vehicle, such as from a CAN-bus of the vehicle, DMS, or the like. In some exemplary embodiments, training of the classifier may be performed prior to performing the described steps. The classifier may be trained with respect to a set of measurement obtained by monitoring the driver. Additionally or alternatively, the classifier may be trained with respect to a set of measurement obtained by monitoring one or more different drivers having a similarity measurement below a threshold to the driver. The classifier may be trained without monitored data of the driver.

On Step 250, a determination whether the driver is capable of operating the vehicle safely may be performed based on the cognitive state of the driver. In some exemplary embodiments, the determination may be performed based on research results of the connection between cognitive state and driving capabilities, brain-computer interface (BCI), determining electroencephalographic (EEG) brain dynamics in lane-keeping driving experiments, or the like. Additionally or alternatively, the determination may be performed based on comparing the cognitive state of the driver with previous cognitive state thereof while being detected as sober, with cognitive state of other people, or the like.

On Step 260, in response to determining that the driver is not capable of safe driving, a responsive action may be applied.

Additionally or alternatively, in response to determining that the driver is not capable of safe driving, Step 210 may be repeated while in Step 212 a different set of stimuli may be determined.

Figure 2B:
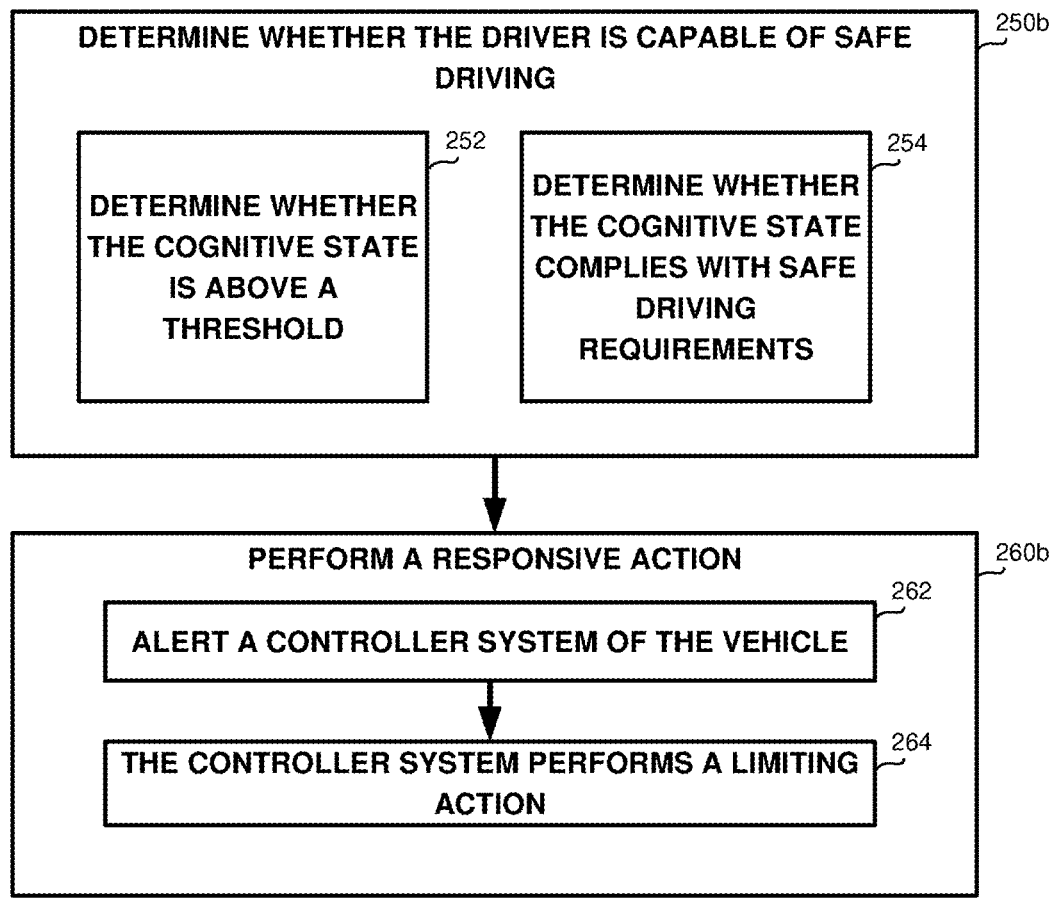

Referring now to FIG. 2B showing a flowchart diagram of a method, in accordance with some exemplary embodiments of the disclosed subject matter.

On Step 250*b*, a determination whether the driver is capable of operating the vehicle safely may be performed based on the cognitive state of the driver.

On Step 252, a determination whether the cognitive state of the driver is above a minimal threshold may be performed. In some exemplary embodiments, the minimal threshold may be determined based on the driver's driving habits when is sober, based on measured cognitive state of the driver when sober, based on cognitive states of other sober drivers with similar properties, such as age, gender, driving experience, or the like. In some exemplary embodiments, the cognitive state may be determined based on the set of features that are derived from measurements of the ocular behavior and ocular responses. The cognitive state may be determined by mapping the set of features to relevant performance levels, such as driving performance. In some exemplary embodiments, a wide range of performance levels may be achieved by utilizing controlled experiments in which the cognitive performance is deliberately degraded. As an example, the cognitive performance may be deliberately degraded by inducing fatigue or by instructing subjects to consume a certain amount of alcohol. In some exemplary embodiments, performance levels, such as driving performance that correlates with cognitive states, may be assessed based on the deviation from the baseline of the ocular responses of the drivers. The baselines may be determined using clustering of the sets of features of driver that operate without a degradation of the performance level.

On Step 254, a determination whether the cognitive state of the driver complies with safe driving requirements may be performed.

On Step 260, a responsive action may be performed in response to determining that the driver is not capable for safe driving. As an example the responsive action may be performed in response to a determination that the cognitive state of the driver is not compatible with safe driving requirements, in response to a determination that the cognitive state is below the minimal threshold, or the like.

On Step 262, a controller system of the vehicle may be alerted. In some exemplary embodiments, the controller system may be a computing device of the vehicle, an autonomous driving system of the vehicle, DMS of the vehicle, or the like.

On Step 264, the controller system may be configured to perform a limiting action. In some exemplary embodiments, the limiting action may comprise activating autonomous driving of the vehicle, limiting a speed of the vehicle, instructing the vehicle to make a safe stop, issuing an alert to a third party, issuing an alert to the driver, or the like.

Figure 2C:
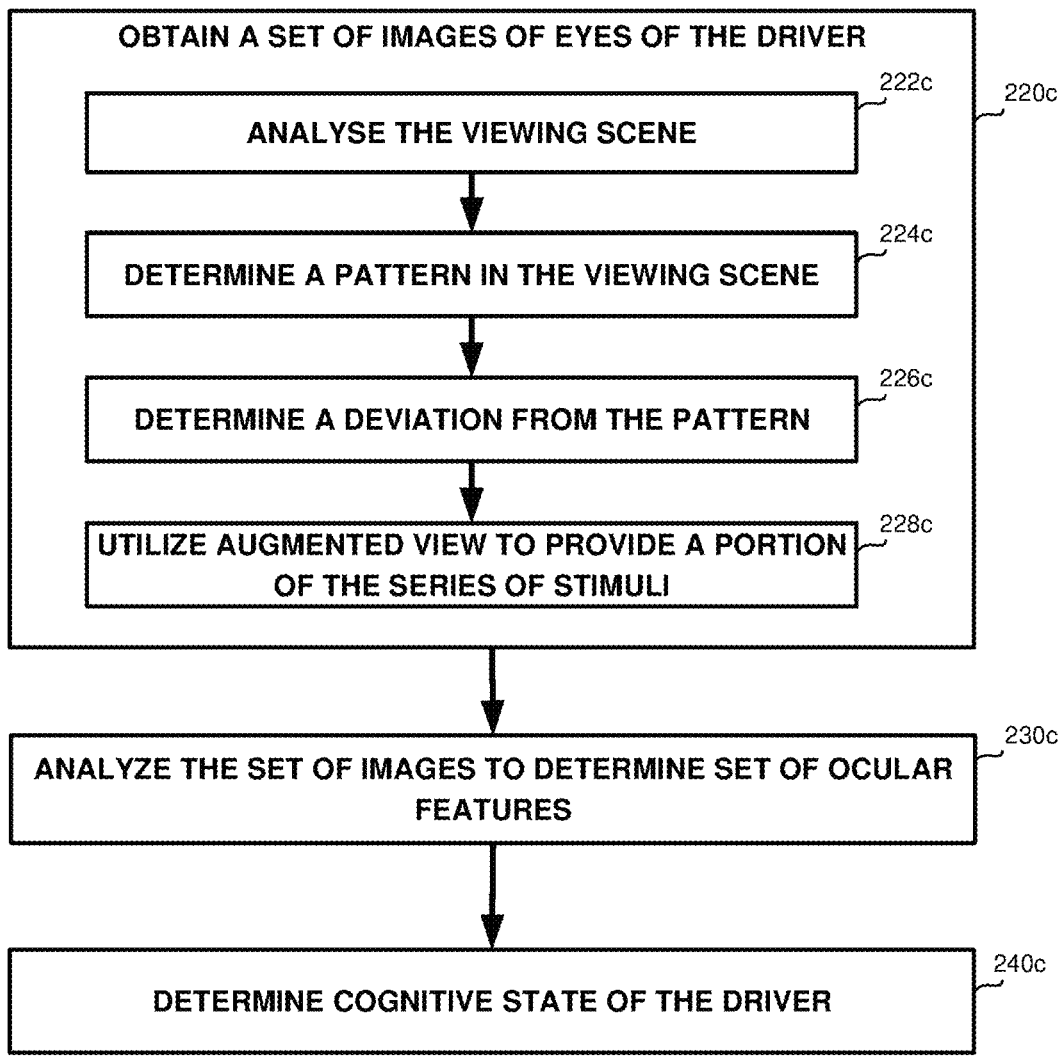

Referring now to FIG. 2C showing a flowchart diagram of a method, in accordance with some exemplary embodiments of the disclosed subject matter.

On Step 220*c*, a set of images of eyes of a driver may be obtained. In some exemplary embodiments, the set of images may be captured while the driver is exposed to a series of stimuli and while the driver is driving a vehicle. In some exemplary embodiments, the series of stimuli may be may be occurring, at least in part, naturally in a viewing scene of the drive while driving the vehicle, the natural noise heard by the driver while driving, or the like.

In some exemplary embodiments, the series of stimuli may comprise a first portion matching a pattern and a second portion deviating from the pattern. The series of stimuli may be configured to induce an ocular response from the eyes.

On Step 222*c*, the viewing scene of the drive, may be analyzed to determine the naturally occurring portion of the series of stimuli. In some exemplary embodiments, a visual sensor may be utilized to capture the viewing scene of the drive and continuously records the view through a vehicle's front windscreen or other windows, such as a dashboard camera, a car Digital Video Recorder (DVR), a driving recorder, Event Data Recorder (EDR), or the like.

On Step 224*b*, the pattern of the stimuli in the viewing scene may be determined. In some exemplary embodiments, the first portion of the series of stimuli may comprise existing visual stimuli in the viewing scene of the driver. The pattern may be determined based on elements in the existing visual stimuli, such as stationary elements within the viewing scene, repetitive elements, or the like.

On Step 226b, a deviation from the pattern indicating stimuli from the second portion of the series of stimuli, may be determined. In some exemplary embodiments, the deviation may naturally occur in the viewing scene, such as missing a repetitive element, a rapid change in the viewing scene, a surprising element, or the like. Additionally or alternatively, the deviation from the pattern may be actively induced, such as using augmented reality improvising a breaking of the pattern, such as mimicking missing a repetitive element, a rapid change in the viewing scene, a surprising element, or the like.

On Step 228b, an augmented view of the viewing scene may be utilized to cause the driver to view the series of stimuli. In some exemplary embodiments, the second portion of the series of stimuli may be dynamically generated using augmented reality to deviate from the pattern in the existing visual stimuli, whereby minimizing intervention on sight of the driver.

On Step 230c, the set of images may be analyzed to determine a set of ocular features corresponding each image.

On Step 240c, a cognitive state of the driver may be determined based on the set of ocular features of the set of images.

Figure 3A:
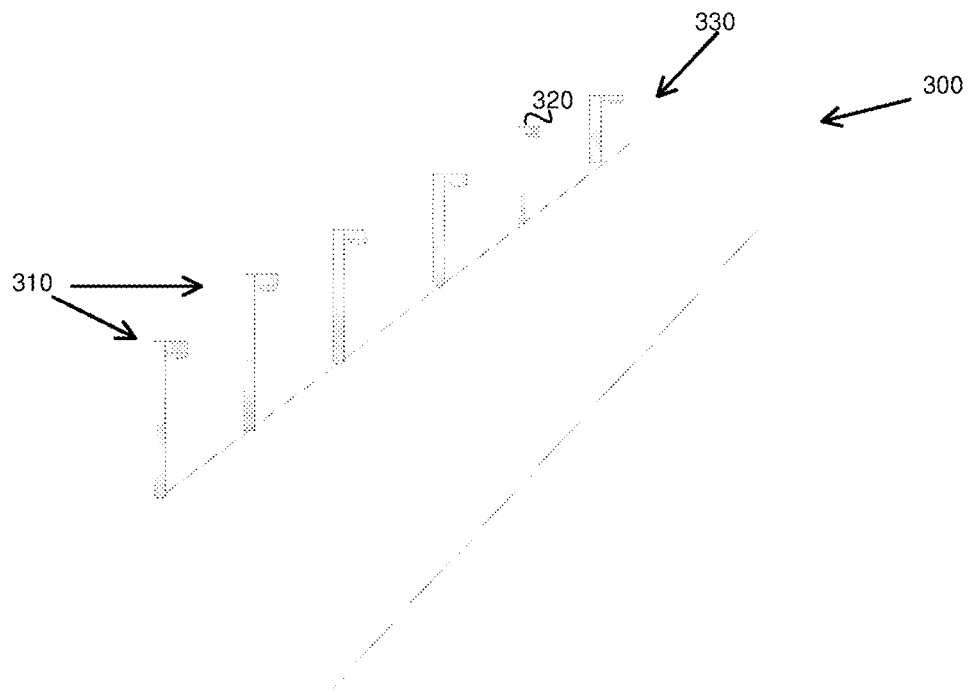
FIGS. 3A-3B show schematic illustrations of an exemplary viewing scene, in accordance with some exemplary embodiments of the disclosed subject matter.

Referring now to FIG. 3A showing a schematic illustration of an exemplary viewing scene, in accordance with some exemplary embodiments of the disclosed subject matter.

In some exemplary embodiments, the driver may passively be exposed to a series of stimuli while driving a vehicle. The series of stimuli may be occurring, at least in part, naturally in a Viewing Scene 300 of the driver, such as seen by the driver from the windshield, the front window, or the like. The series of stimuli may be configured to induce an ocular response from the eyes of the driver.

In some exemplary embodiments, Viewing Scene 300 may be captured by a visual sensor of the vehicle that captures the viewing scene of the driver. Viewing Scene 300 may be analyzed to determine the naturally occurring portion of the series of stimuli.

In some exemplary embodiments, the series of stimuli may comprise a first portion matching a pattern and a second portion deviating from the pattern. The pattern may be a naturally occurring pattern, such as a repetitive element, a stable element along the road, or the like. The first portion of the series of stimuli may comprise existing visual stimuli in Viewing Scene 300. The pattern may be determined based on elements in the existing visual stimuli of Viewing Scene 300. As an example, Series of Stimuli 330 may comprise a series of consecutive Electricity Poles 310 with the same distance from each other.

In some exemplary embodiments, deviating stimuli, e.g. the second portion of the series of stimuli may be also naturally occurring in the environment, e.g. in Viewing Scene 300. As an example, Electricity Pole 320 may be smaller than the other Electricity Poles 310.

Figure 3B:
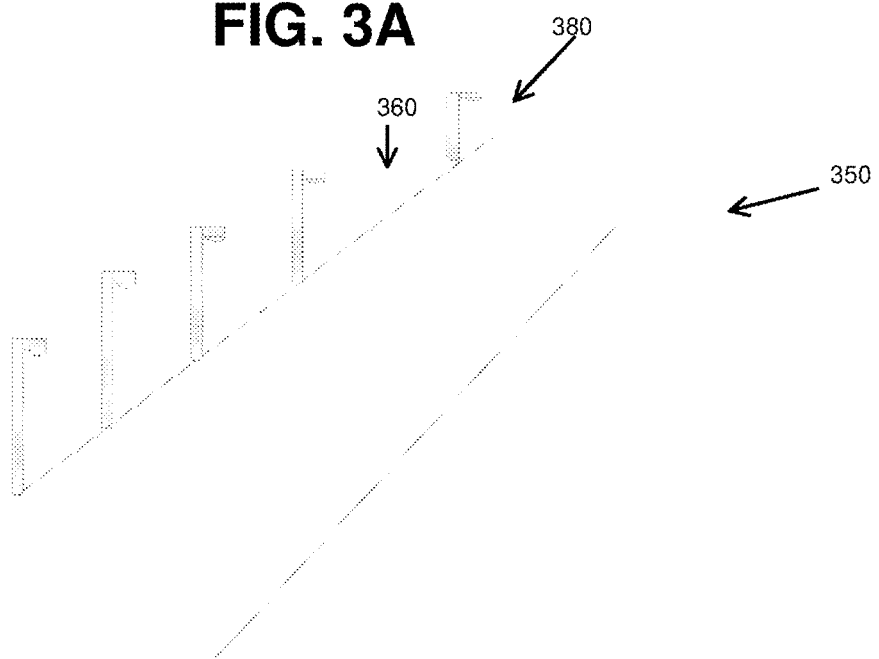

Referring now to FIG. 3B showing a schematic illustration of an exemplary viewing scene using augmented reality, in accordance with some exemplary embodiments of the disclosed subject matter.

In some exemplary embodiments, the series of stimuli may be partially naturally occurring, in a manner that Viewing Scene 300 may comprise only stimuli that match the pattern. As an example, Viewing Scene 300 may comprise Electricity Poles 310 including Electricity Pole 320 in substantially similar size and distance from the others.

In order to enable a deviation from the pattern, an Augmented View 350 of Viewing Scene 300 may be provided to the driver to cause her to view the series of stimuli with the pattern and the deviation therefrom. Augmented View 350 may be provided using augmented reality tools, such as augmented reality eyeglasses, augmented reality windshield screen, HoloLens capable of projecting holograms on the road, or the like.

In some exemplary embodiments, Viewing Scene 300 may be obtained by a forward-looking camera, that is operable to assess the existence of at least some such patterns within the scene viewed by the driver. Additionally or alternatively, Viewing Scene 300 may be obtained the camera and analyzed by the cognitive state determination system (Such as System 100 of FIG. 1).

In some exemplary embodiments, the pattern may be determined based on elements in the existing visual stimuli of Viewing Scene 300, such as a portion of Series of Stimuli 330 that comprises a series of 4 consecutive Electricity Poles 310 with the same distance from each other. Additionally or alternatively, the existence of such pattern along the road may be assessed based on previous rides by the same vehicle or by other vehicles employing the system.

The second portion of the series of stimuli, e.g. the deviation from the pattern, may be dynamically generated using the augmented reality tools to deviate from the pattern in the existing visual stimuli, whereby minimizing intervention on sight of the driver. As an example, Electricity Pole 320 may be removed from Augmented View 350, to generate a deviated stimuli of Missing Pole 360, that follows the pattern of the 4 consecutive Electricity Poles 310. The generated Series of Stimuli 380 may comprise repetitively naturally viewed 4 consecutive Electricity Poles 310, followed by dynamically generated Missing Pole 360.

In some exemplary embodiments, the module that assess the cognitive state of the driver may preferably utilize ocular responses to such patterns, thereby enhancing the efficacy and effectiveness of the system without increasing the load on the driver.

Figure 4A:
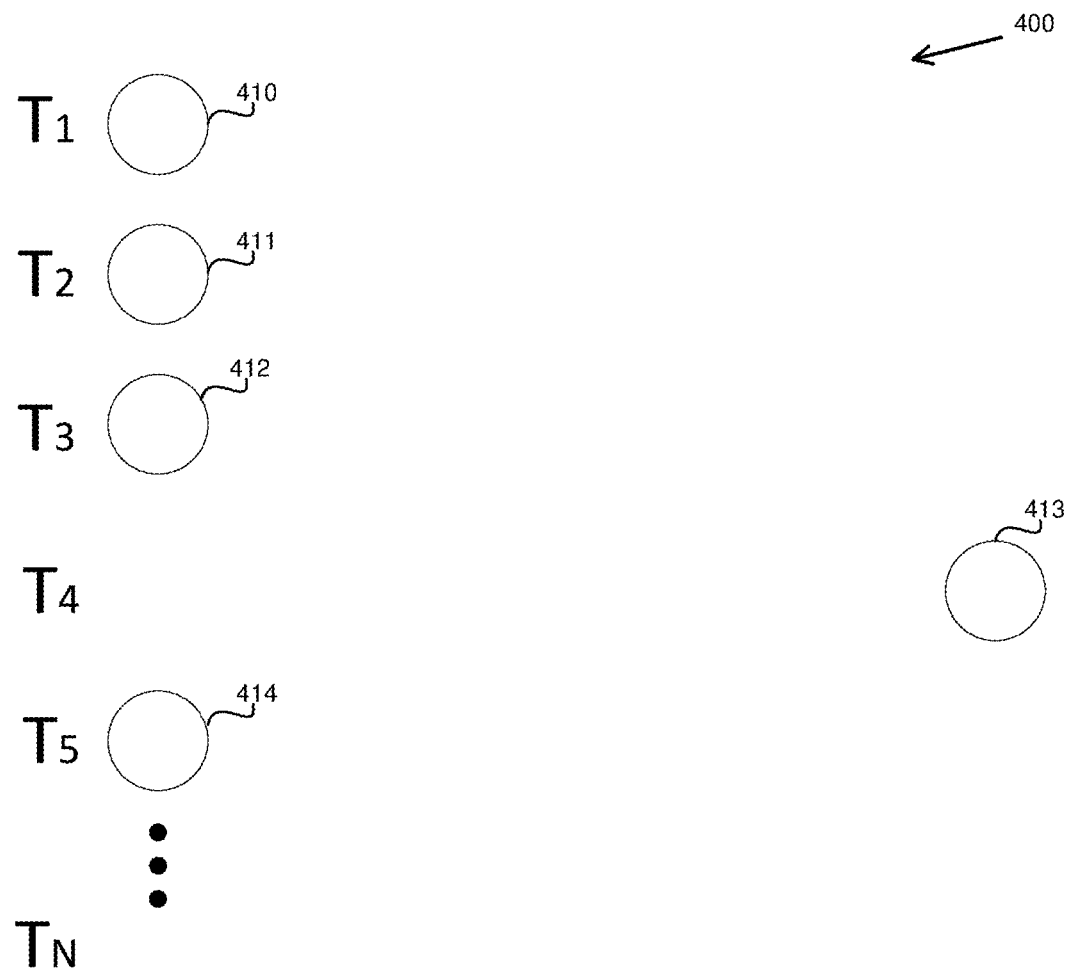
FIGS. 4A-4B show schematic illustrations of a stimuli pattern and deviation therefrom, in accordance with some exemplary embodiments of the disclosed subject matter.

Referring now to FIG. 4A showing a schematic illustration of a stimuli pattern and deviation therefrom, in accordance with some exemplary embodiments of the disclosed subject matter.

FIG. 4A illustrates an oddball paradigm that allow to assess aspects of the cognitive status of the drivers and their capabilities with respect to the driving task.

In some exemplary embodiments, Pattern 400 may comprise similar instances of Object 410 may abruptly appear either on the right side of the screen (e.g., 410, 411, 412, 414, etc.) or the left side of the screen (e.g., 413), during regular time intervals, such as every 500 milliseconds, every 2000 milliseconds, every 3000 milliseconds, or the like. In the majority of the cases (e.g., 80%) the object appears on the same side, thereby allow the driver to infer an existence of a pattern. At a fraction of the times (e.g., 20%) the object appears in opposite side of the screen, thereby breaking the pattern. As a result, Pattern 400 may illustrate the breaking of such pattern as the first 3 objects (e.g., 410, 411, 412) appear on the left hand side, the than fourth (413) on the right hand side.

Figure 4B:
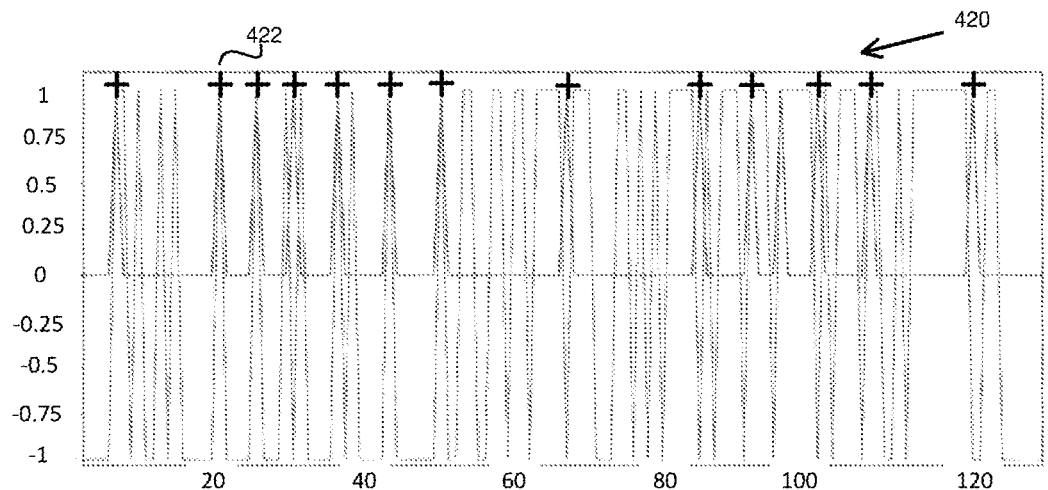

Referring now to FIG. 4B showing a schematic illustration of a stimuli pattern and deviation therefrom, in accordance with some exemplary embodiments of the disclosed subject matter.

In one embodiment, Series of Stimuli 420 is an actual time series of stimuli used in one of the conducted experiments in accordance with Pattern 400 presented in FIG. 4A. In Series of Stimuli 420, +1 indicates appearance on the right-hand side and −1 on the left hand side. The + symbols indicate "surprises", or "oddballs": instances in which the pattern of the last few stimuli is broken.

Figure 4C:
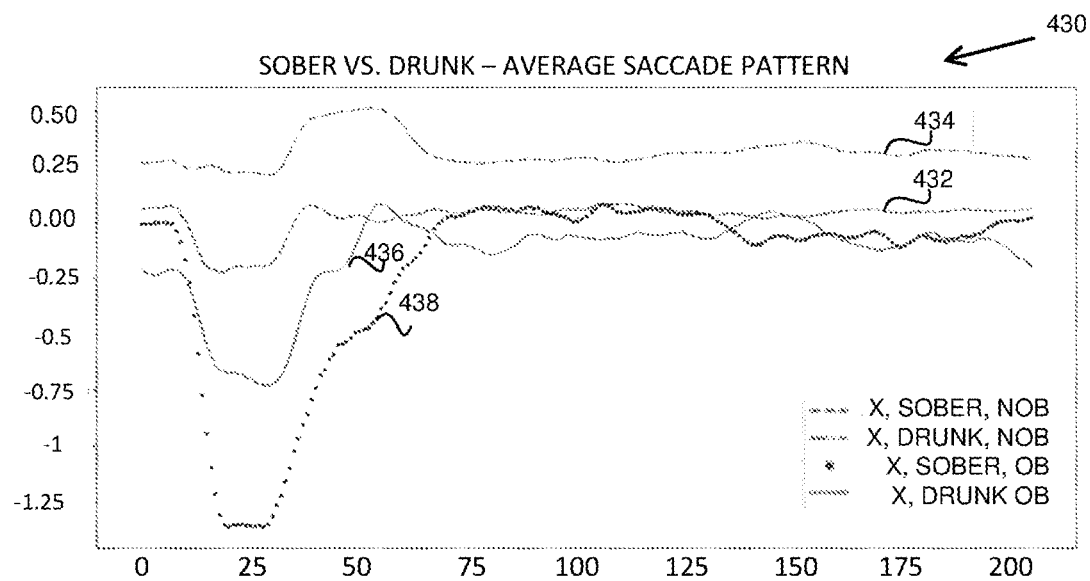
FIG. 4C shows a schematic illustration of a graph representing a deterioration of a cognitive state of a driver, in accordance with some exemplary embodiments of the disclosed subject matter.

Referring now to FIG. 4C showing a schematic illustration of average ocular responses to stimuli pattern and deviation therefrom for sober and drunk subjects, in accordance with some exemplary embodiments of the disclosed subject matter.

In some exemplary embodiments, occasional breaking of an expected temporal or spatial pattern may be configured to induce a surprise response that induces a brain activity. As an example, the brain activity may be manifested by a pulse referred to as P300 in the EEG pattern that is manifested by an identifiable ocular response, such as pupil dilation, changes in the saccade patterns, or the like.

Graph 430 illustrates the average ocular responses to oddballs vs. non-oddballs stimuli of Series of Stimuli 420 presented in FIG. 4B, for sober and drunk subjects. Graph 430 represents an average saccade pattern of the subject, for sober and drunk subjects. Line 432 represents an average saccade pattern of sober subject for non-oddball stimuli. Line 434 represents an average saccade pattern of drunk subject for non-oddball stimuli. Line 436 represents an average saccade pattern of sober subject for oddball stimuli. Line 438 represents an average saccade pattern of drunk subject for oddball stimuli.

It may be noted that the difference between the ocular responses, reflected by the time series of the saccades along the horizontal direct of sober vs. drunk is much more pronounced for the oddballs.

Figure 4D:
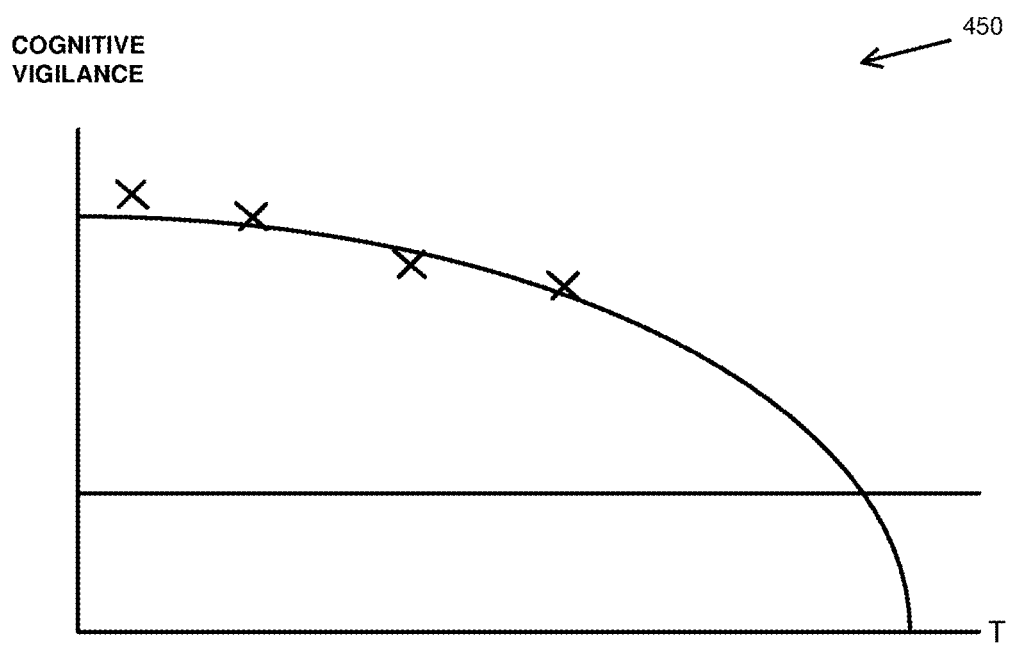
FIG. 4D shows a schematic illustration of average ocular responses to stimuli pattern and deviation therefrom for sober and drunk subjects, in accordance with some exemplary embodiments of the disclosed subject matter.

Referring now to FIG. 4D showing a schematic illustration of a graph representing a deterioration of a cognitive state of a driver, in accordance with some exemplary embodiments of the disclosed subject matter.

In some exemplary embodiments, the cognitive state of the driver may deteriorate over time, with or without the affection of alcohol and drug consumption, fatigue, or the like. Such deterioration may be more sever when the cognitive state is affected by alcohol and drug consumption, fatigue, or the like.

In accordance with some exemplary embodiments, Graph 700 represents a schematic model of the deterioration of the cognitive state of the driver over time, e.g., due to fatigue.

Figure 5:
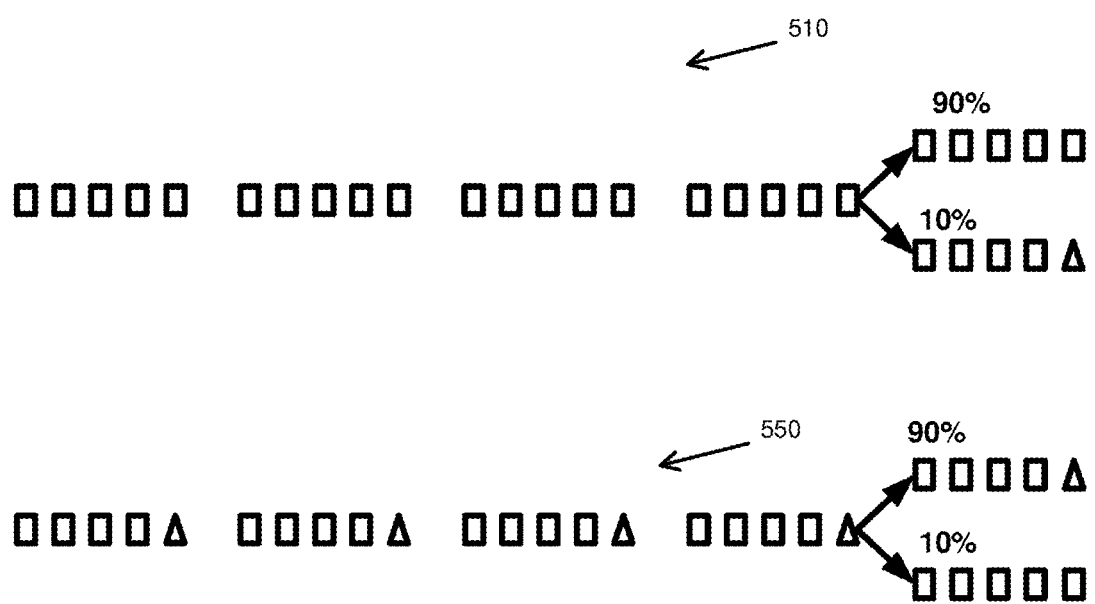
FIG. 5 shows a schematic illustration of exemplary series of stimuli, in accordance with some exemplary embodiments of the disclosed subject matter.

Referring now to FIG. 5 showing a schematic illustration of exemplary series of stimuli, in accordance with some exemplary embodiments of the disclosed subject matter.

In some exemplary embodiments, the pattern in series of stimuli may comprise a pattern of sub-patterns. The deviation in the pattern of patterns may be induced by applying a different sub-pattern. The series of stimuli may comprise a set of sub-series of stimuli. The deviation from the pattern may occur a sub-series of stimuli, having a different pattern from the other sub-series.

Paradigm 510 represents a stimuli series that comprises a set of series of 5 instances at regular intervals, with a longer interval between these series. The pattern in Paradigm 510 comprises multiple series of 5 identical instances, known as "local patterns", which may be a majority of the set, such as about 90% of the series. The deviation from the "local" patterns is represented as a substantially similar series in which the fifth instance in the series is different than the rest of the instances, which may be a minority of the set, e.g., about 10% of the series, thereby creating, in this case, a "global" deviation from the basic pattern.

Paradigm 550 represents a stimuli series that comprises a set of series of 5 instances at regular intervals, with a longer interval between these series. The pattern in Paradigm 550 comprises multiple series of 4 identical instances and a fifth instance which is different than the first 4 instances, such that each "local" interval comprise a deviation from the basic pattern. The pattern series may be majority of the set, such as about 90% of the series. The deviation from the pattern is represented as a substantially similar series in which the five instances are identical, which may be a minority of the set, e.g., about 10% of the series, thereby creating, in this case, a "global" deviation from the basic pattern.

In both cases, after presenting several series matching the pattern, one deviated series may be induced as a "surprise".

It may be noted that identifying deviation from global regularity that include local regularities may require more cognitive resources, and therefore may provide an indication for the existence of these resources and the capabilities of the driver. In this case, ocular responses may provide a good indication with respect to the "surprises", and thereby allow to infer and assess the cognitive state of the driver.

Figure 6:
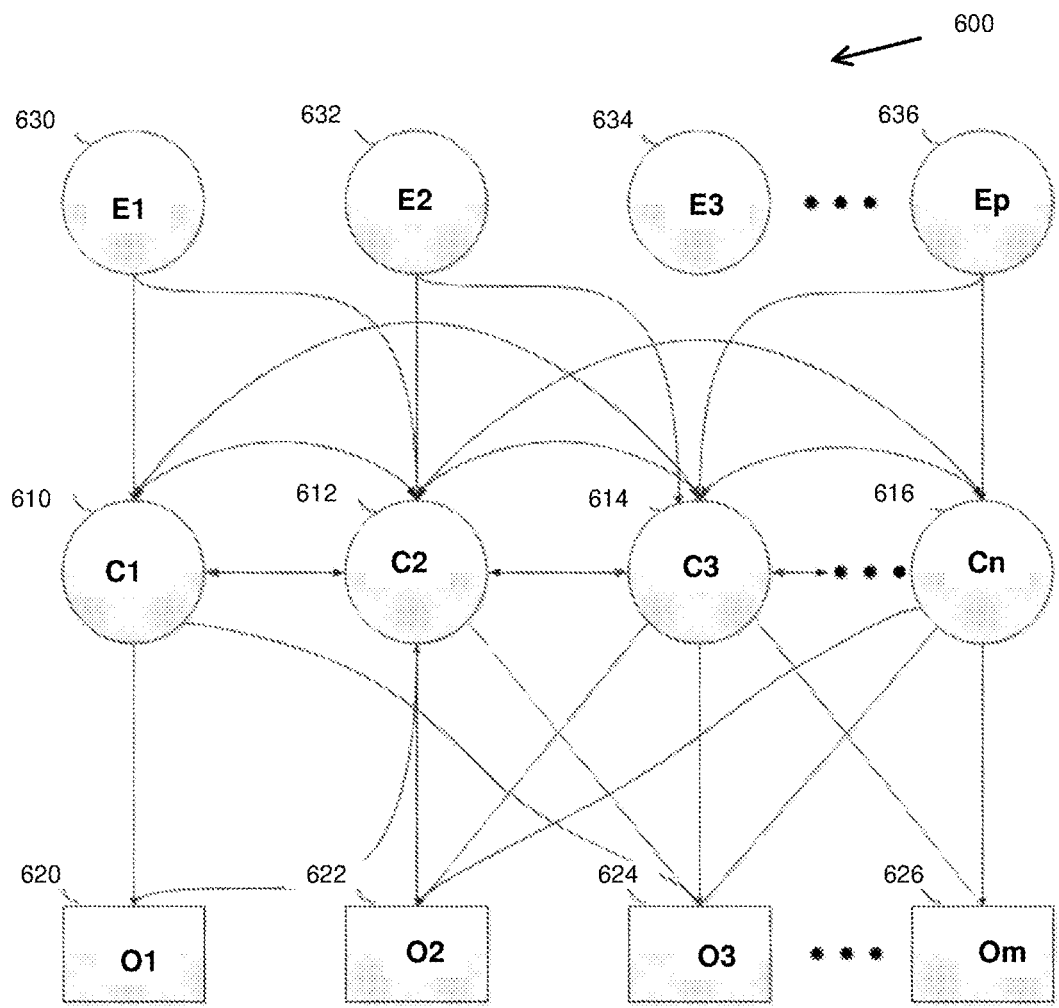
FIG. 6 shows a schematic illustration of Hidden Markov Models (HMMs) for assessing cognitive state of a driver, in accordance with some exemplary embodiments of the disclosed subject matter.

Referring now to FIG. 6 showing a schematic illustration of the usage of HMMs for inferring cognitive state of a driver sates from visible indicators, in accordance with some exemplary embodiments of the disclosed subject matter.

Figure 7A:
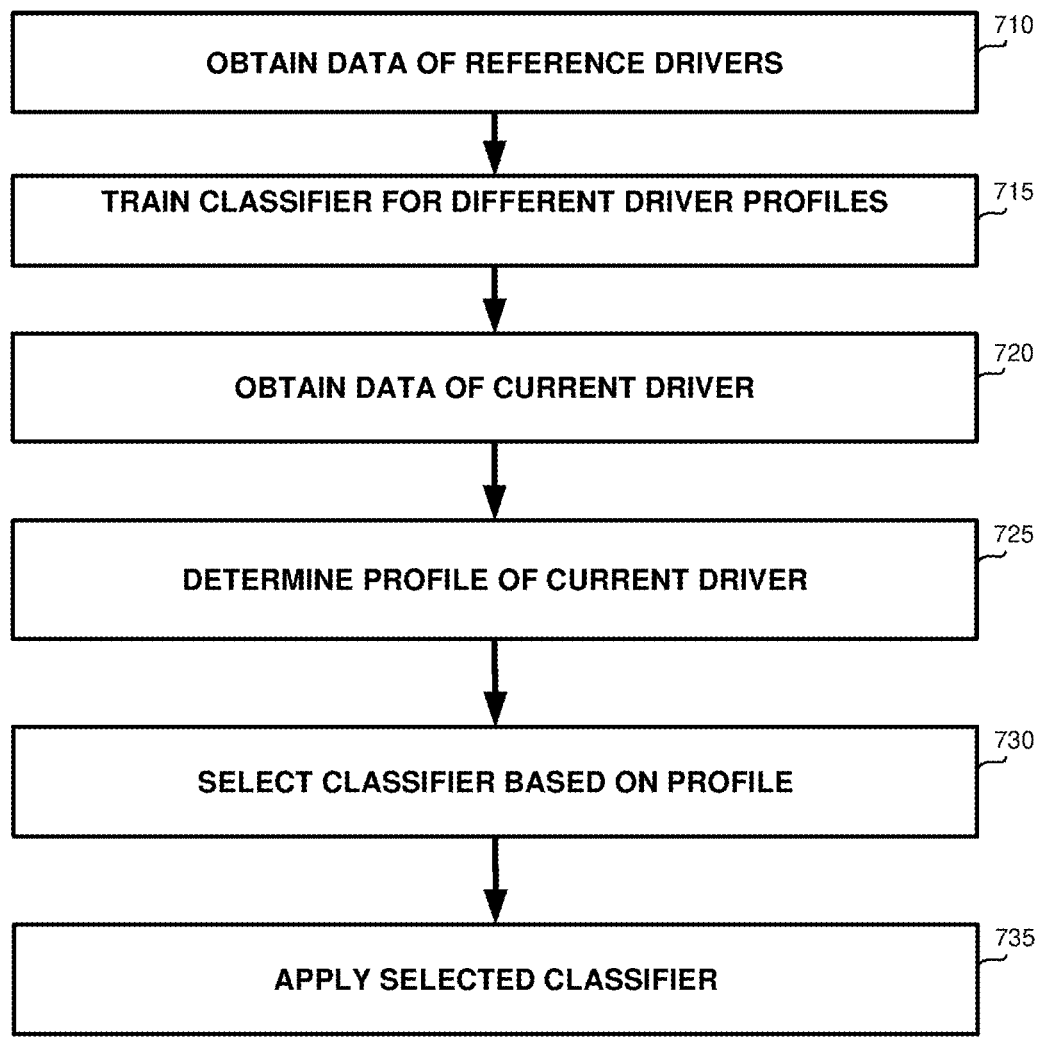

In some exemplary embodiments, HMM 600 may comprise a plurality of Cognitive States C1, C2, C3 . . . Cn (reference numeral 610, 612, 614 and 616) each of which may reflect engagement in various mental activities, such as scanning objects and threats within the visual field, daydreaming, engagement in non-driving activities such as texting, or the like. Additionally or alternatively, HMM 600 may comprise a plurality of Visible States O1, O2, O3 . . . Om (reference numeral 620, 622, 624 and 626), each of which may be represented using sets of indicators regarding the driver's engagement and receptivity, based on the ocular responses of the driver. Additionally or alternatively, HMM 600 may comprise a plurality of environmental states E1, E2, E3 . . . Ep (reference numeral 630, 632, 634 and 636). The probability to obtain a visible state Oi while the driver is in a cognitive state Cj may be represented as P(Oi|Cj). The probability of being in a cognitive state Ck at time T is derived from the previous cognitive states at time T-1, T-2, T-3 . . . and the known environmental states E1, E2, E3 . . . Ep. By applying HMM 600, a prediction of the cognitive state of the driver at a certain time point (e.g., the cognitive state with the higher probability), may be determined based on the previous determined cognitive states of the driver, in accordance with the visible indicators of the ocular responses and environmental parameters. Referring now to FIG. 7A showing a flowchart diagram of a method, in accordance with some exemplary embodiments of the disclosed subject matter.

On Step 710, data of reference drivers may be obtained. In some exemplary embodiments, the reference drivers may be different drivers that the system may have an access to their data, such as drivers utilizing the disclosed system for monitoring the cognitive state, drivers in related databases, such as biometric databases, criminal databases, or the like. In some exemplary embodiments, the data may comprise demographic data of the reference drivers, such as age, acuity of sight, gender, weight, driving license information, or the like. The data may further comprise information about driving patterns of the reference drivers, such as driving style, experience, average driving speed, obeying road rules and signs, recorded traffic violations, lane keeping, driving habits in wide turnings, or the like. The data may further comprise cognitive properties of the reference drivers, such as cognitive levels and capabilities, ocular responses to different events, assessed physical and mental condition at a specific time (such as fatigue, alertness, mood, destructions, or the like), the dynamics of ongoing attention allocation, or the like. The data may further comprise information regarding consumption of drugs, alcohol, smoking, or the like.

Additionally or alternatively, the data may comprise experimental data regrading subjects with different properties, such as measured cognitive states for different subjects in response to different stimuli, ocular responses of the subjects to different stimuli, ocular responses of sober subjects vs. ocular responses of subjects under the effect of drugs or alcohol, or the like.

On step 715, classifiers may be trained for different drivers. In some exemplary embodiments, the reference drivers may be clustered based on their properties. Each classifier may be trained with respect to a different group or cluster of drivers. The classifier may be trained to predict cognitive state based on a set of ocular features associated with application of a series of stimuli on the driver.

On Step 720, data of a current driver may be obtained. In some exemplary embodiments, the data may comprise demographic data of the current driver, driving patterns, cognitive abilities, drug and alcohol consumption habits, or the like.

On Step 725, a profile of the current driver may be determined. In some exemplary embodiments, the profile of the current driver may be determined based on the clustering of the reference drivers, based on similarity with other drivers, or the like. Additionally or alternatively, the profile of the current driver may be determined based in a similarity measurement between the driver and a cluster of reference drivers being above a predetermined threshold, such as above 80%, above 90%, above 95%, or the like.

On Step 730, a classifier may be selected based on the profile. In some exemplary embodiments, the classifier trained for the relevant cluster or group of reference drivers. The classifier may be trained without monitored data of the driver, by transfer learning applied on the reference drivers.

On Step 735, the selected classifier may be applied to determine the cognitive state of the driver. In some exemplary embodiments, the classifier may be applied on the set of ocular features of the set of images. Additionally or alternatively, the classifier may be applied on the one or more statistical measurements of the set of ocular features of the set of images.

Figure 7B:
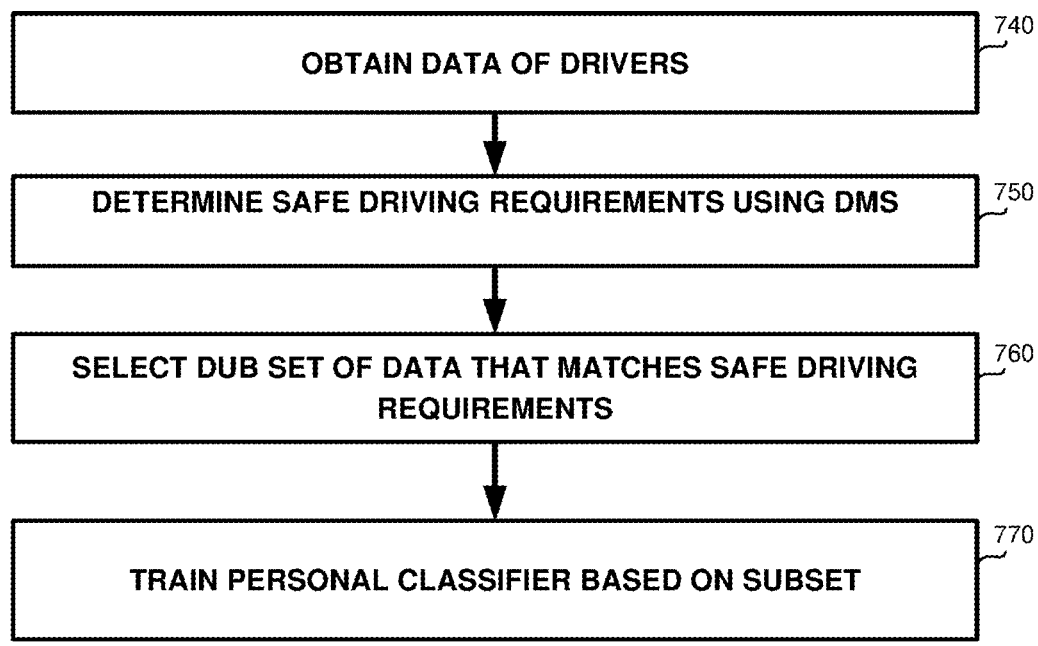

Referring now to FIG. 7B showing a flowchart diagram of a method, in accordance with some exemplary embodiments of the disclosed subject matter.

On Step 740, data of a driver may be obtained. In some exemplary embodiments, the data may comprise properties of the driver, such as demographic properties, such as age, gender, weight, or the like. Additionally or alternatively, the data may comprise driving data of the driver, as obtained from a computing device of the vehicle, such as from a CAN-bus of the vehicle, DMS, or the like. The driving data may comprise speed data in different conditions, attentiveness, speed, complying with traffic rules, or the like. Additionally or alternatively, the data may comprise alcohol and drugs consumption habits.

On step 750, safe driving requirements may be determined. In some exemplary embodiments, the safe driving requirements may be determined based on regulatory requirements, based on DMS data, based on environmental parameters, such as road conditions, or the like.

On Step 760, a subset of the data of the driver that relates to safe driving requirements may be selected. In some exemplary embodiments, the influence of each type of data of the driver on the safe driving requirements may be analyzed and determined.

On Step 770, a personalized classifier may be trained based on the selected subset.

Figure 8:
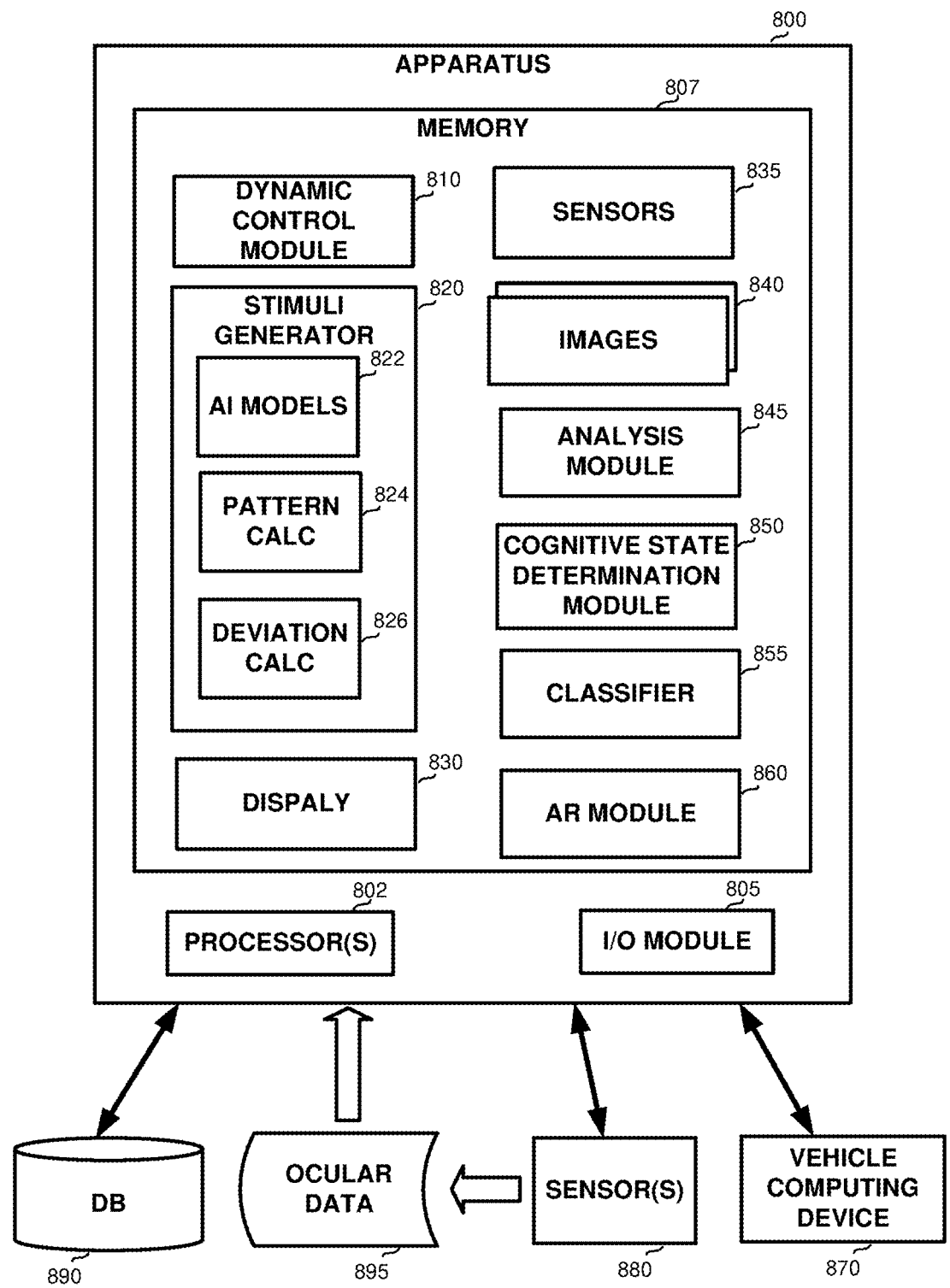
FIG. 8 shows a block diagram of an apparatus, in accordance with some exemplary embodiments of the disclosed subject matter.

Referring now to FIG. 8 showing a block diagram of an apparatus, in accordance with some exemplary embodiments of the disclosed subject matter.

An Apparatus 800 may be configured to continuously monitor the cognitive state of a driver (not shown) pertain to driving, in accordance with the disclosed subject matter.

In some exemplary embodiments, Apparatus 800 may comprise one or more Processor(s) 802. Processor 802 may be a Central Processing Unit (CPU), a microprocessor, an electronic circuit, an Integrated Circuit (IC) or the like. Processor 802 may be utilized to perform computations required by Apparatus 800 or any of it subcomponents.

In some exemplary embodiments of the disclosed subject matter, Apparatus 800 may comprise an Input/Output (I/O) module 805. I/O Module 805 may be utilized to provide an output and to receive input from one or more sensors, such as for example Sensor(s) 880, from a computing device of a vehicle, such as Computing Device 870, from external databases, such as Database 890, or the like.

In some exemplary embodiments, Apparatus 800 may comprise Memory 807. Memory 807 may be a hard disk drive, a Flash disk, a Random Access Memory (RAM), a memory chip, or the like. In some exemplary embodiments, Memory 807 may retain program code operative to cause Processor 802 to perform acts associated with any of the subcomponents of Apparatus 800.

In some exemplary embodiments, Apparatus 800 may be configured to enable passive monitoring and an active probing of the driver's status, thereby continuously monitoring continuously the cognitive state of the driver.

In some exemplary embodiments, Apparatus 800 may comprise a Dynamic Control Module 810 that is configured to utilize a spectrum of stimuli operable to induce a set of ocular responses that provide indications regarding the cognitive state of the driver. In some exemplary embodiments, Dynamic Control Module 810 may be configured to utilize a Stimuli Generator 820 for generating a series of stimuli to be applied on the driver. The series of stimuli may comprise a first portion matching a pattern and a second portion deviating from the pattern. The method of claim 1, wherein the second portion deviating from the pattern deviates from the pattern in at least one of a timing of stimulus, a spatial location of stimulus, a magnitude of stimulus, and a type of stimulus.

Additionally or alternatively, Stimuli Generator 820 may be configured to generate the stimuli based on a paradigm of breaking an expected temporal and/or spatial pattern, in a manner operable to induce certain brain activities. Stimuli Generator 820 may utilize Pattern Calculator 824 in order to generate such pattern, and Deviation Calculator 826 in order to generate a breaking of the pattern such as by generating an oddball stimulus, oddball set of stimuli, or the like.

In some exemplary embodiments, Stimuli Generator 820 may be configured to apply AI Models 822 to provide an optimal set of stimuli to the driver. AI Models 822 may be applied on features of the driver, features of drivers with similar properties, environmental features, such as weather, road conditions, vehicle properties, or the like. AI Models 822 may comprise control engineering, reinforcement learning, particle filters, transfer learning, or the like. Stimuli Generator 820 may be configured to exploit big data and transfer learning paradigm to utilize data from other drivers in order to enhance the accuracy of the assessment of the cognitive state of the driver.

In some exemplary embodiments, Stimuli Generator 820 may be configured to utilize human cognitive system characteristics in order to determine the stimuli to be applied on the driver. Human cognitive system characteristics may comprise three features of the human cognitive system: (1) its strive to reduce dimensionality and information; (2) its ability to produce predictions concerning the world; and (3) its reliance on top-down and bottom-up attention for 1 and 2. Stimuli Generator 820 may be configured to may be configured to generate a reduced stimuli containing only the relevant information to induce an adaptive response, such as location of the relevant stimulus, its movement vector and its speed.

In some exemplary embodiments, Dynamic Control Module 810 may be configured to display the series of stimuli on a Display 830 in accordance with the type of the stimuli. Display 830 may be an output device that is located in the vehicle and directed at the driver. As an example, visual stimuli, may be displayed on a display or a screen facing the driver. As another example, audible stimuli may be provided by an audio means in the vehicle, such as a radio, a microphone, a computing device, or the like. As yet another example, haptic stimuli may be applied by a tactile means touching the driver, such as sensors on the steering wheel, the driver seat, the seat belt, or the like.

In some exemplary embodiments, the series of stimuli may be occurring, at least in part, naturally in a viewing scene of the driver. The viewing scene of the driver may be captured using a visual sensor (such as using Sensors 880), a dashcam, a camera on the windshield, or the like. Stimuli Generator 820 may be configured to determine the naturally occurring portion of the series of stimuli. In some exemplary embodiments, the whole series of stimuli may be naturally occurring in the viewing scene of the driver. Pattern Calculator 824 and Deviation Calculator 826 may be configured to determine a pattern in viewing scene and a breaking thereof, and provide the pattern and deviation to Analysis Module 845 to determine the respective ocular features in accordance with the naturally occurring series of stimuli. Additionally or alternatively, only a portion of the series stimuli may be naturally occurring. An Augmented Reality Module 860 may be utilized to generate an augmented view of the viewing scene to cause the driver to view the series of stimuli. Stimuli Generator 820 may be configured to determine which part of the stimuli is naturally occurring, and which stimuli should be added, and instruct Augmented Reality Module 860 accordingly. Augmented Reality Module 860 may be configured to utilize augmented reality techniques in accordance with systems of the vehicle in order to project the added stimuli in the viewing scene of the driver. Additionally or alternatively, Augmented Reality Module 860 may be configured to generate an augmented reality view in accordance with the viewing scene of the driver and display it using Display 830.

In some exemplary embodiments, one or more Sensors 835 may be utilized to capture a set of Images 840 of the eyes of the driver during the application of the series of stimuli. Sensors 835 may be located in the vehicle and facing the driver. Sensors 835 may comprise an eye tracker, inward looking camera, a thermographic camera, IR sensors, multispectral camera, operable to assess physiological parameters such as body temperature and pulse and to penetrate sunglasses, or the like. Additionally or alternatively, Images 840 may be obtained from other sensors or systems of the vehicle, such as Sensors 880, Vehicle Computing Device 870, a DMS connected to Vehicle Computing Device 870, or the like.

In some exemplary embodiments, Analysis Module 845 may be configured to analyze Images 840 to determine a set of ocular features corresponding to each image. The set of ocular features may comprise features related to saccade of the eyes of the driver, sight direction, eyes movement speed, size of pupils, pupils dilation, constriction responses of the eyes, symmetry measurements between the eyes, facial expressions in a proximity of the eyes, eyebrow movements, rate of blinks, movements of the head or the neck of the driver, or the like.

In some exemplary embodiments, a Cognitive State Determination Module 850 may be configured to determine based on the set of ocular features of Images 840, a cognitive state of the driver. Cognitive State Determination Module 850 may be configured to determine the cognitive state based on one or more statistical measurements of the set of ocular features of Images 840, such as ICA, PCA, entropy measurements, STD, average, or the like, of the determined values of each ocular feature. Additionally or alternatively, each ocular feature may be treated as layer in a multilayer network, and analyzed accordingly, using network analysis techniques. Each layer may be weighted based on the relation between the respective ocular response and the cognitive state, such as based on previous experience, based on literature data, or the like.

In some exemplary embodiments, Cognitive State Determination Module 850 may be configured to utilize temporal data and location data in order to assess the prior probability of alcohol and drug consumption, enhance the sensitivity of the analysis or the like. The temporal and location data may comprise location of the vehicle over time, closeness to pubs and liquor stores, time of the drive and probability of overlapping with popular drug and alcohol consumption times, such as weekends, late night hours, or the like. The temporal and location data may be obtained from a GPS of the vehicle, from location sensors of a mobile device of the driver, from one or more databases of such information, such as Database 890, online databases, or the like.

Additionally or alternatively, Cognitive State Determination Module 850 may be configured to perform the analysis based on properties of the driver. In some exemplary embodiments the identity of the driver may be established, using face detection or other biometric measures based on data obtained from Sensors 880, such as face features, fingerprints on the steering wheel, or the like. Additionally or alternatively, the identity of the driver may be determined based on data from a computing device f the driver, Vehicle Computing Device 870, or the like.

Additionally or alternatively, Cognitive State Determination Module 850 may be configured to perform the determination of the cognitive state based on habits of the driver with relation to consumption of alcohol and drugs may be used in the likelihood assessment, based on driving patterns of the driver, or the like. Such data may be determined based on previous ocular data of the driver (e.g., stored by Apparatus 800 or similar apparatuses in Ocular Data DB 895), may be determined based on data obtained from Database 890 or other databases, such as a database of police tickets in the area, social networks, based on driving habits of the driver as obtained from a computing device of the vehicle (870), or the like.

In some exemplary embodiments, Cognitive State Determination Module 850 may be configured to determine based on the cognitive state of the driver, whether the driver is capable of operating the vehicle safely, such as by determining whether the cognitive state of the driver is above a minimal threshold, whether the cognitive state of the driver is compatible with safe driving requirements, or the like. In response to a determining that the cognitive state is below the minimal threshold, is not compatible with safe driving requirements, Apparatus 800 may be configured to perform a responsive action, such as alerting a controller system of the vehicle, via Vehicle Computing Device 870, alerting the driver using one or more methodology in the vehicle, activating autonomous driving of the vehicle via Vehicle Computing Device 870, limiting a speed of the vehicle, instructing the vehicle to make a safe stop, issuing an alert to a third party via a mobile device of the driver, such a friend, a trustee, the authorities, or the like.

In some exemplary embodiments, Cognitive State Determination Module 850 may be configured to apply a Classifier 855 on the set of features or statistical measurements thereof to determine the cognitive state. In some exemplary embodiments, Classifier 855 may be trained with respect to a set of measurement obtained by monitoring the driver, such as driving habits of the driver when being affected by alcohol or drug, when being tired, or the like, compared with driving habits of the driver when being sober. Additionally or alternatively, Classifier 855 may be trained with respect to a set of measurement obtained by monitoring one or more different drivers similar features to the driver, such as the same age, the same gender, the same driving habits, or the like. Classifier 855 may be trained without monitored data of the driver.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
   obtaining a set of images of eyes of a driver, wherein the set of images is captured while the driver is exposed to a series of stimuli and while the driver is driving a vehicle, wherein the series of stimuli comprises a first portion matching a pattern and a second portion deviating from the pattern, wherein the series of stimuli is configured to induce an ocular response from the eyes, wherein the series of stimuli is occurring, at least in part, naturally in a viewing scene of the driver;
   analyzing the set of images to determine a set of ocular features corresponding each image; and
   determining, based on the set of ocular features of the set of images, a cognitive state of the driver.

2. The method of claim 1 further comprises utilizing a visual sensor to capture the viewing scene of the driver, and analyzing the viewing scene to identify a naturally occurring portion of the series of stimuli.

3. The method of claim 1, wherein the series of stimuli is partially naturally occurring, and wherein the method further comprises providing an augmented view of the viewing scene to cause the driver to view the series of stimuli.

4. The method of claim 1, wherein the first portion of the series of stimuli comprises existing elements in the viewing scene of the driver, wherein the pattern is determined based on the elements in the existing visual stimuli, wherein the second portion of the series of stimuli is dynamically generated using augmented reality to deviate from the pattern in the existing visual stimuli, whereby minimizing intervention on sight of the driver.

\* \* \* \* \*